United States Patent
Zhu et al.

(10) Patent No.: US 6,891,154 B2
(45) Date of Patent: May 10, 2005

(54) AMINO ACID SEQUENCE PATTERN MATCHING

(75) Inventors: Weimin Zhu, Toronto (CA); John Marshall, Toronto (CA); Christopher Smith, Milton (CA); Rulin Zhang, Brampton (CA)

(73) Assignee: Syn X Pharma, Inc., Ontario (CA)

( * ) Notice: Subject to any disclaimer, the term of this patent is extended or adjusted under 35 U.S.C. 154(b) by 25 days.

(21) Appl. No.: 10/231,660

(22) Filed: Aug. 30, 2002

(65) Prior Publication Data

US 2004/0041089 A1 Mar. 4, 2004

(51) Int. Cl.[7] .......................... B01D 59/44; H01J 49/00; G01N 33/00; C12Q 1/70; C12Q 1/68
(52) U.S. Cl. .................. 250/282; 250/281; 436/89; 436/94; 435/5; 435/6
(58) Field of Search .................. 250/282, 281, 250/288; 435/5, 6; 436/89, 94

(56) References Cited

U.S. PATENT DOCUMENTS

| | | | | |
|---|---|---|---|---|
| 5,470,753 A | * | 11/1995 | Sepetov et al. | 436/89 |
| 5,538,897 A | * | 7/1996 | Yates et al. | 436/89 |
| 6,017,693 A | * | 1/2000 | Yates et al. | 435/5 |
| 6,582,965 B1 | * | 6/2003 | Townsend et al. | 436/89 |
| 6,677,114 B1 | * | 1/2004 | Schneider et al. | 435/4 |

* cited by examiner

Primary Examiner—John R. Lee
Assistant Examiner—Kalimah Fernandez
(74) Attorney, Agent, or Firm—McHale & Slavin, P.A.

(57) ABSTRACT

A method for locating pattern matches in amino acids by use of various and sequential filters capable of determining inner sample pattern matches, inner group pattern matches, and word matching for purposes of further analysis or data mining. Filters include the use of a scoring scheme, comparison of scan numbers versus sequence of common ions to be MS/MS, and daughter ion subtraction for obtaining pattern match candidates.

16 Claims, 6 Drawing Sheets

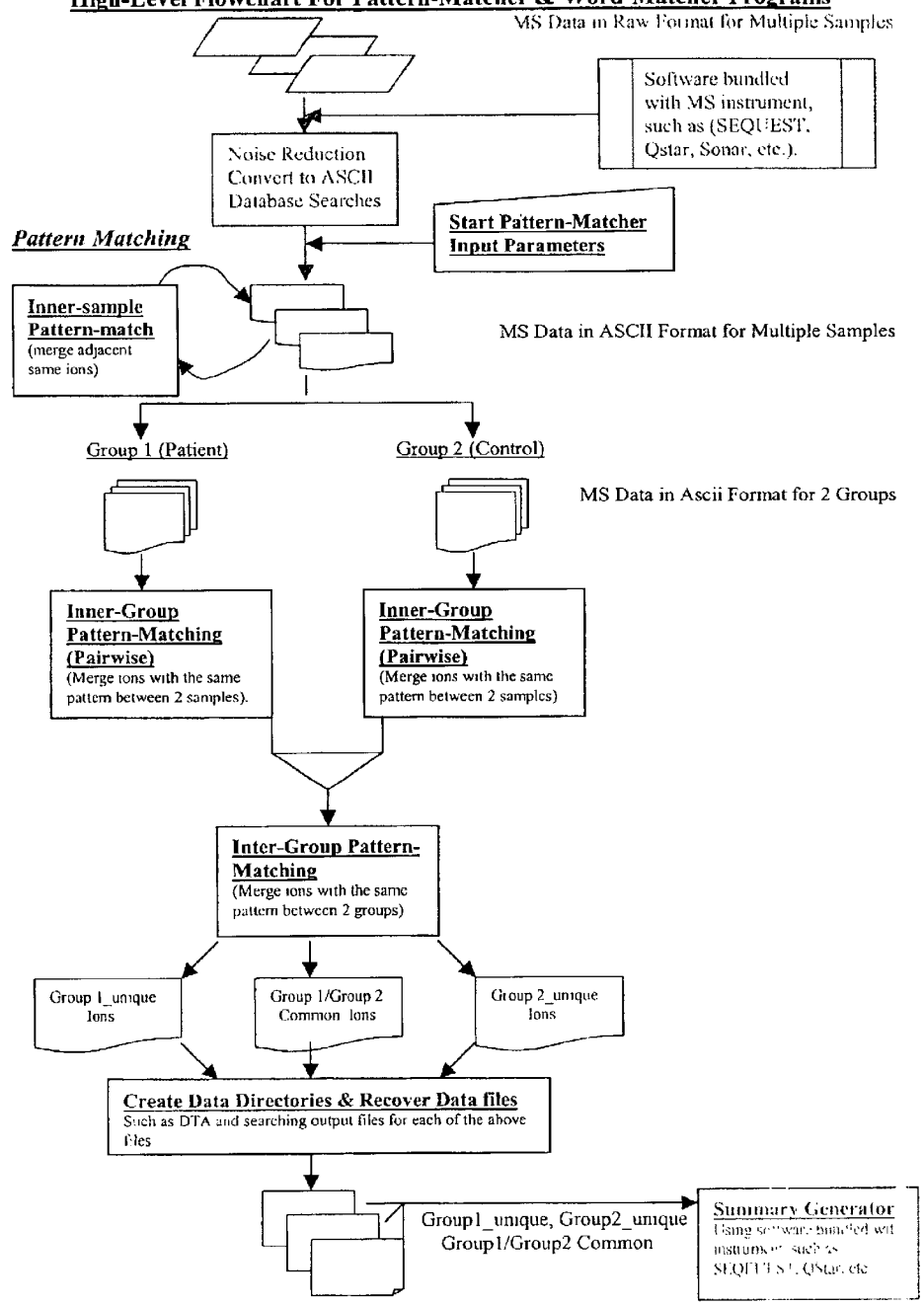

*Inter-Group Pattern-Matching:*

AMINO ACID SEQUENCE PATTERN MATCHING

FIELD OF THE INVENTION

This invention relates generally to methods for determining amino acid composition, and more specifically, to sequence discovery between sample groups through a method of detecting matching patterns.

BACKGROUND INFORMATION

The use of mass spectrometers, including those which perform tandem mass spectrometry (MS/MS), are known to be useful in determining amino acid sequences. Currently available spectrometers are capable of presenting a wide mass range of ions, MS/MS providing daughter ion analysis of a single parent mass. The parent ion is selected by use of a frequency of applied supplemental voltage and the daughter ions are ejected by scanning. From this it is possible to obtain a reconstructed parent ion spectrum from a large number of successive daughter ion scans. Parent ions may also be excited by pulses of energy at their resonant frequency, the daughter ions may be ejected from the ion trap at their resonant frequency. The available means for determining unique amino acid sequence lacks specificity.

Ion trap mass spectrometers, such as those manufactured by the Finnigan Corporation, employ an electrostatic field in which ions are formed and stored by use of a quadrupole trapping field. In a tandem quadrupole ion trap mass spectrometer, ions are formed and stored in an ion trap and then mass selected by a mass analyzer wherein the ions are dissociated by means of a collision induced dissociation with a gas or surface and the fragment ions are analyzed by means of a mass or energy analyzer. During the operation of a tandem quadrupole ion trap mass spectrometer product ions, or daughter ions, are produced by isolating a precursor ion, or parent ion, which has undergone the collision induced dissociation. The collision induced dissociation can occur by applying an excitation waveform between end cap electrodes. A radio frequency voltage generator can be used to supply an RF voltage between the end caps and a ring electrode which provides the quadrupole field for trapping ions. A supplemental RF generator is coupled to the end caps to resonate trapped ions at their axial resonant frequencies. These excited ions undergo fragmentation upon the colliding with a surface or buffer gas, such as helium, placed within the buffer trap. An end cap is perforated to allow unstable ions in the field of the ion trap to exit and be detected by an electron multiplier. The magnitude and/or frequency of the fundamental RF voltage can be varied for providing mass selection. The goal is to isolate a particular ion.

Commercially available quadrupole ion trap mass spectrometers capable of tandem mass spectrophotometry are capable of isolating a single parent ion by inducing a collision dissociation to produce daughter ions which are resonantly ejected from an ion trap for detection by a mass-selective instability scan. Alternative techniques that should also be noted include the application of simultaneous excitation voltages or waveforms across the end caps.

After any characteristic daughter ions in the trap have been ejected, application of a parent ion resonant excitation waveform, can result in some parent ions that are resonantly ejected resulting in false positive readings during the detection of the characteristic daughter ions.

Sample mass may be analyzed by any combination of ionization and mass spectrometer. The ionization method may include, but is not limited to such methods as electron ionization, chemical ionization, fast atom bombardment, desorption chemical ionization, plasmadeorption, thermospray, atmospheric pressure chemical ionization, MALDI or electrospray ionization (ESI). Principally the ionization method will be MALDI or ESI. Prior art mass spectrometer formats are known to be useful either singly or in various combinations for use in analyzing translation products. These formats may include, but are not limited to, ionization (I) techniques, including but not limited to matrix assisted laser desorption (MALDI), continuous or pulsed electrospray (ESI) and related methods (e.g., IONSPPAY or THERMOSPRAY), or massive cluster impact (MCI); these ion sources can be matched with detection formats including linear or non-linear reflection time-of-flight (TOF), single or multiple quadropole, single or multiple magnetic sector, Fourier Transform ion cyclotron resonance (FTICR), ion trap, and combinations thereof (e.g., ion-trap/time-of-flight). For ionization, numerous matrix/wavelength combinations (MALDI) or solvent combinations (ESI) can be employed.

With regard to the mass spectrometer, per se, there are several types of tandem mass spectrometers that could be used to generate the patterns of MS/MS spectra that are the substrate for the program. These mass spectrometers generate both parent ions in the +1 (MALDI and ESI) and the +2, +3, +4 etc charge state (ESI). The program takes the charge state of the parent into consideration as part of the data associated with the parent ion. The types of mass analyzer mass analyzers include the quadropole, octopole, ion trap or QUISTOR, time of flight (TOF) Time of Flight with reflectron, the Fourier transformed ion cyclotron resonance (FTICR also called FTMS), magnetic and electromagnetic sector.

The tandem mass spectrometer mass consist of the homogenous or heterogenous combination of two or more of any of these devices in any order (Hybrid instrument). The fragmentation method may include post source decay of the parent ion or its fragment, or collision-activated or collision-induced decomposition of the parent ions, or fragment ions, or metastable ions with a relatively immobile target such as gas molecules or other parent or fragment ions, or photons or electrons or solid objects. The combinations may preferentially include the quadropole or octopole ion trap, the Quadropole-Quadropole (DC and rf or rf only)-TOF, the ion trap-FTMS, the TOF-TOF, the ion trap-TOF, or the TOF-PSD-TOF. The signal resulting from the instrument may be mathematically transformed or filtered.

In view of this, sequence determination of an unknown protein or peptide from mass spectral data can be difficult due to the voluminous number of possible sequences consistent with the molecular weight of the amino acid. Multiple samples result in readings that are unacceptable for most applications due to offsets in samples, preparations, device manufacture, noise filtration, technician sample handling, and so forth. Further, recent advancements in amino acid synthesis have allowed the generation of millions of peptide and protein sequences.

Thus, what is needed in the art is a method of analyzing the voluminous amounts of data that is being produced by such devices.

SUMMARY OF THE INVENTION

The present invention satisfies this need through a method of determining unique amino acid sequences between two groups of samples as analyzed by mass spectrometer, such as a quadrupole ion trap. MS data from multiple samples is received from an MS ion trap, the data being normalized and may include noise reduction. MS data (dta) is provided in an ASCII format. The data may include noise reduction of the MS as a filter setting forth data files (dta). The Raw data is placed into an Inner-sample pattern match performed by merging same ions to form a first group (patient) and a second group (control). Each group is then pattern matched pairwise by merging ions with the same pattern between two samples taken from each group, to form an inter-group pattern match. The pattern provides a first group of unique ions, a second group of unique ions, and a third group having common ions between the first and second group. This is used to create data directories for use with the data files. The software bundled with the MS unit, such as SEQUEST, can then be used for word matching. In this manner an Inter-group comparison is performed for protein matching (multiple ions) and peptide matching (single ions).

In operation, samples are first prepared wherein daughter ions ejected having a particular Dalton range for each DTA sample are merged and the DTA's represented by a single charge state. Parent ions are also merged by scan numbers and the differences of each parent ion mass drop thereby creating a working file for each of the samples which contain data of all DTA's.

Each working file is queried to obtain the parent mass ($M_{qi}$) and charge state ($C_{qi}$) for each parent ion ($Q_i$) and a target working file is then queried to obtain target DTA list ($T_1$–$T_m$) having a parent mass ($M_{t1}$–$M_{tm}$) drop in the range of $M_{qi} \pm 1.5$ Dalton and where their charge states ($C_{t1}$–$C_{tm}$) is the same as $C_{qi}$.

The parent ion is compared with each of the daughter patterns, the daughter ions that match are removed and the use of a scoring system is used to record each match. The scoring system provides a cumulative score; Q_ratio (matched/Total_Query ratio); T_ratio (matched/Total_Target ratio) and t_score (3*((Q ratio+T_ratio)/2)*Rs) where Rs is the acceptable ratio (in %) of matched over total.

The common ions (sample12_common) having matched candidates between $Q_i$ and $T_j$ are recorded, and unmatched candidates are separated into separate files (sample1_unique) and (sample2 unique), the samples are compared to obtain pair matches of parent mass and charge state. The matches are then clustered and the daughter ion patterns are compared within each of the clusters, calculating the ratio of the matched sample #/Total sample # (Rc) wherein the ion will be included in a final group common list if Rc$\geq$Rm.

A single file can then be constructed naming Groupx_whole (uniques+commons) for each file which contains DTA names(s), parent mass, charge state, and all daughter ions. DTA directories are then constructed based on the above files to recover all the DTAs with different charge states, recover original data format for each DTA, recover original file name for each DTA, and create supporting files for a SEQUEST or similar type search for further filtering. Groups can then be summarized on protein names to generate files: a. Group1_unique with_name, b. Group2 unique_with_name, c. Group1_unique_without name, d. Group2_unique_without_name; wherein Group_unique without_name list is used for optional databases searches, and Group_unique_with_name list is used directly for further analysis such as data mining.

An objective of the invention is to provide a method of finding unique protein species between groups of samples provided through mass spectrometry.

Another objective of the invention is to disclose an algorithm for subtracting of common ions between ion samples providing a base for optional database searches for use in further analysis.

Another objective of the invention is to teach the use of ion subtraction between two samples by taking advantage of daughter ion pattern in MS2 spectrum and scan numbers for parent ions.

Still another objective of the invention is to teach the use of ion subtraction with multiple filters in sequence.

Still another objective of the invention is to disclose the use of a scoring system and/or matching ratio for locating of common ions.

Another objective of the invention is to disclose the use of a word-matcher.

Other objectives and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

BRIEF DESCRIPTION OF THE DRAWINGS

FIG. 1A is a flow chart for the pattern matcher program of the instant invention;

DETAILED DESCRIPTION

Figure 1B:
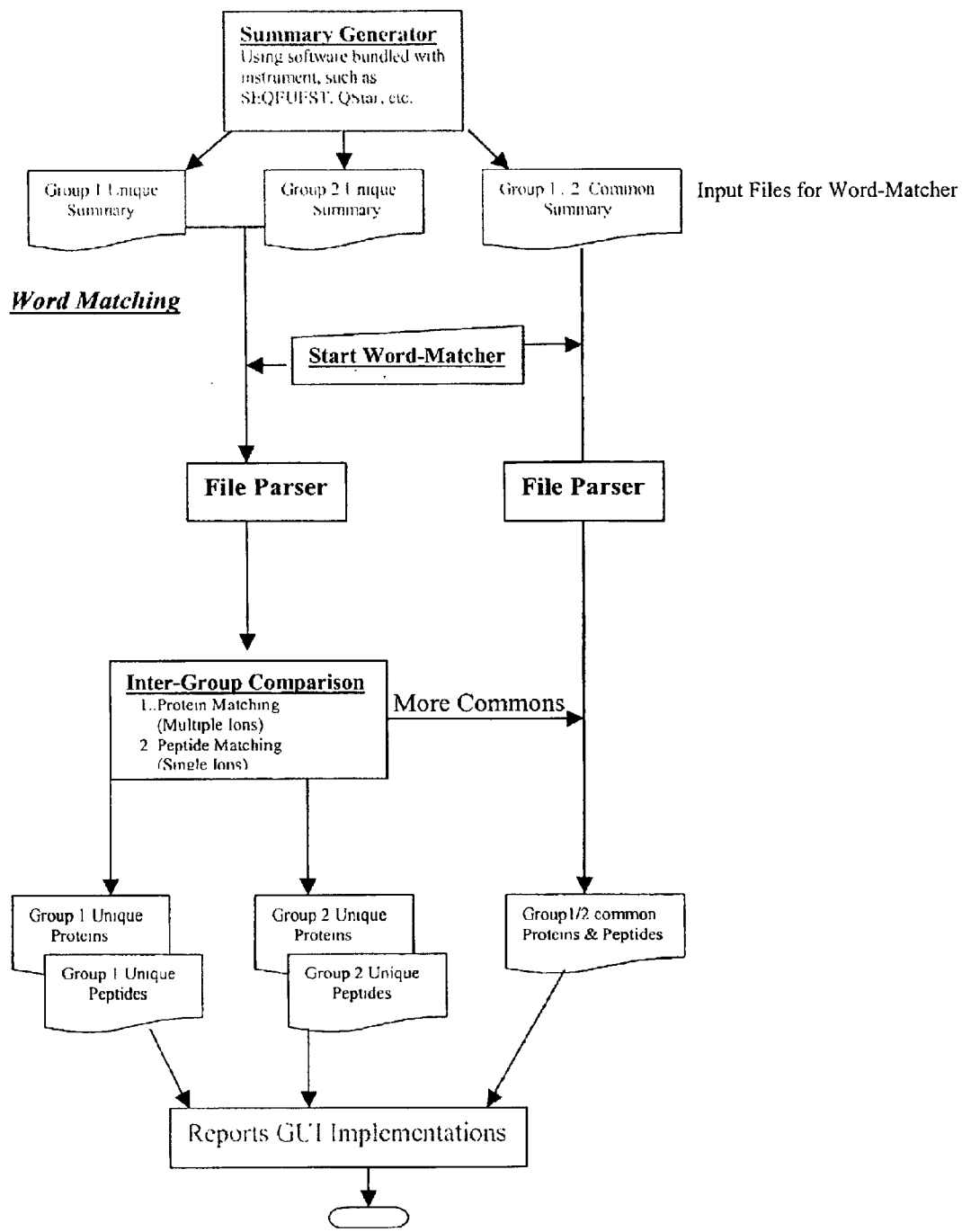
FIG. 1B is a continuation of the flow chart of FIG. 1A.
Figure 2:
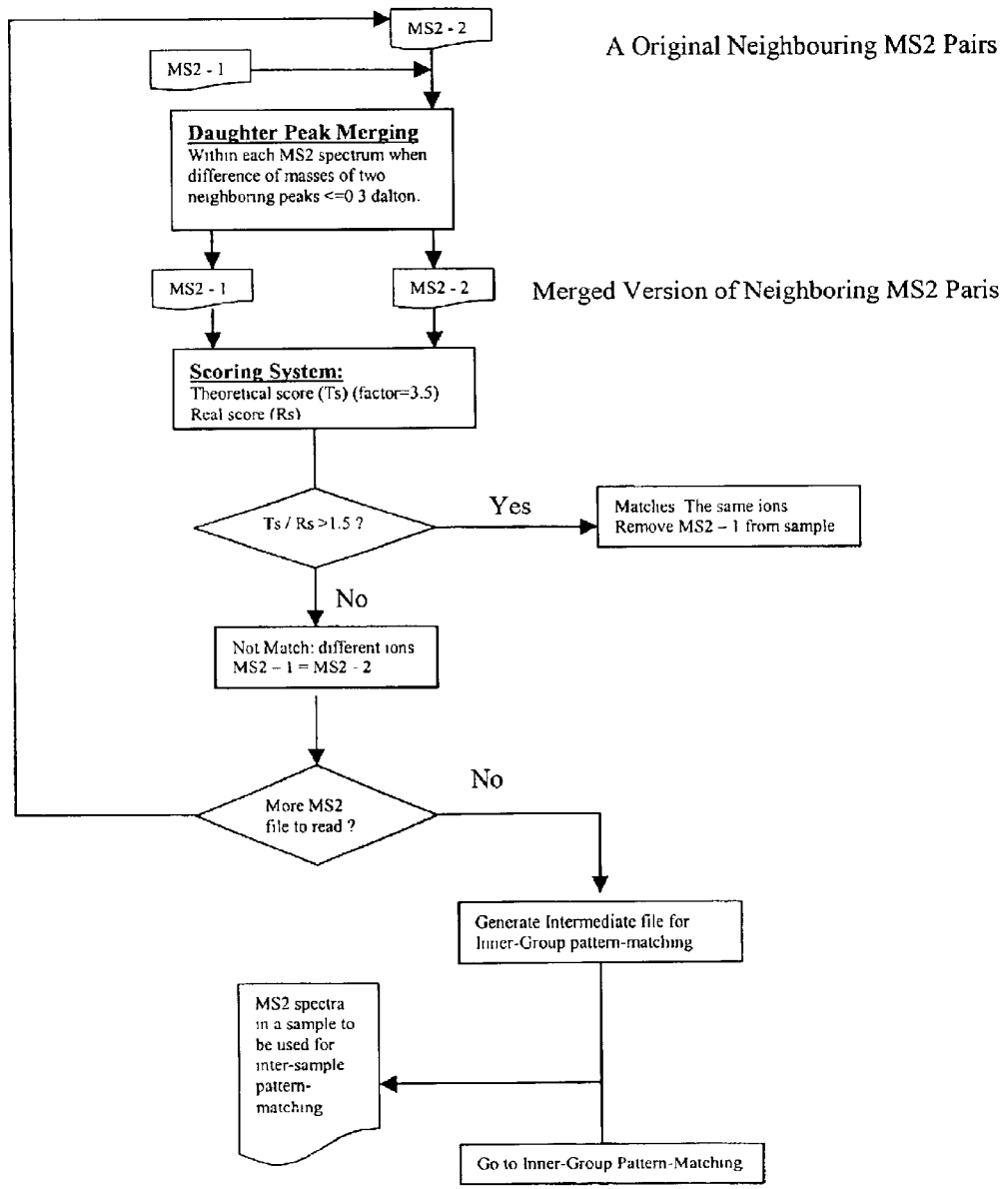
FIG. 2 is a flow chart of inner sample pattern matching.
Figure 3:
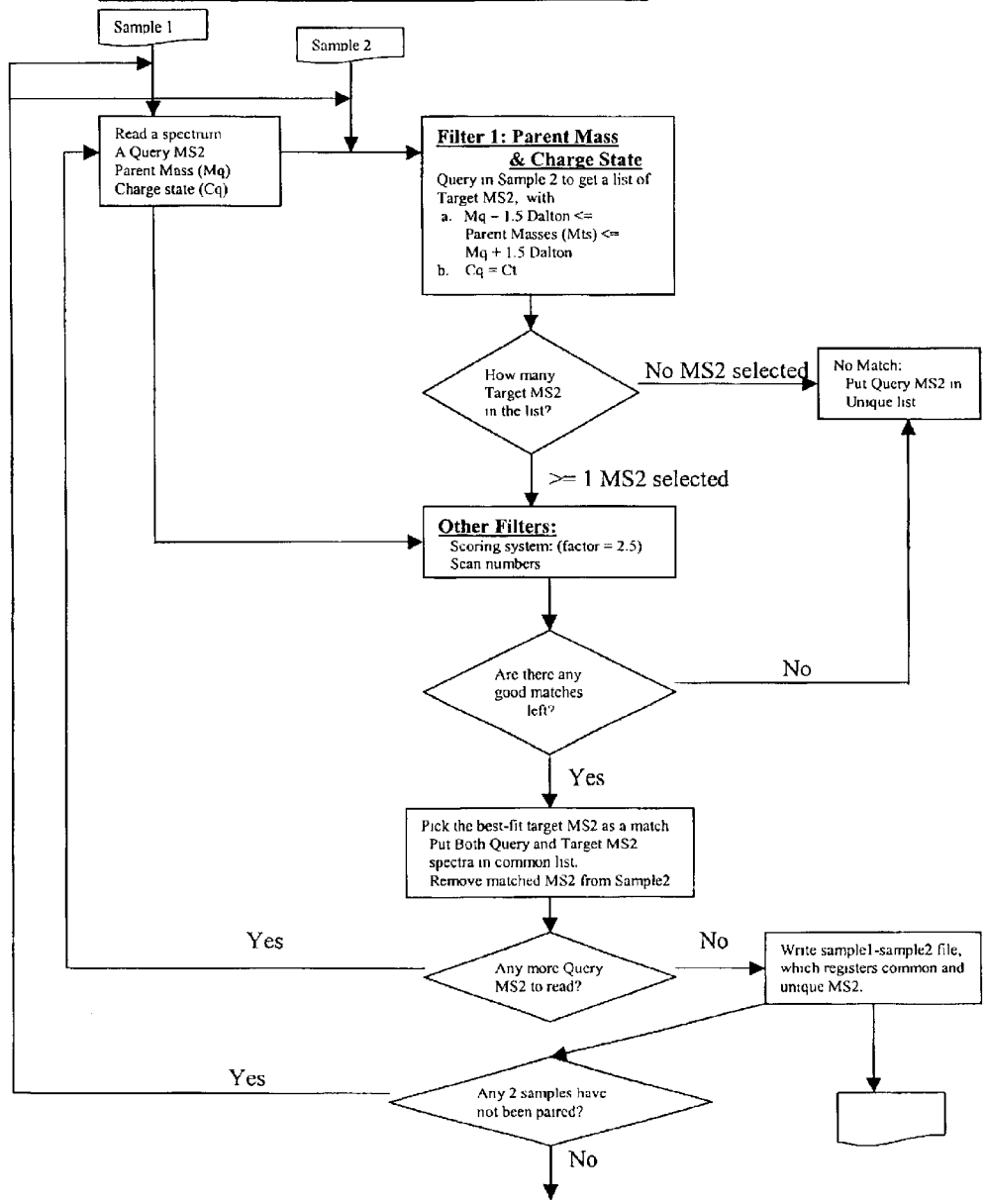
FIG. 3 is a flow chart of inner group pattern matching.
Figure 4:
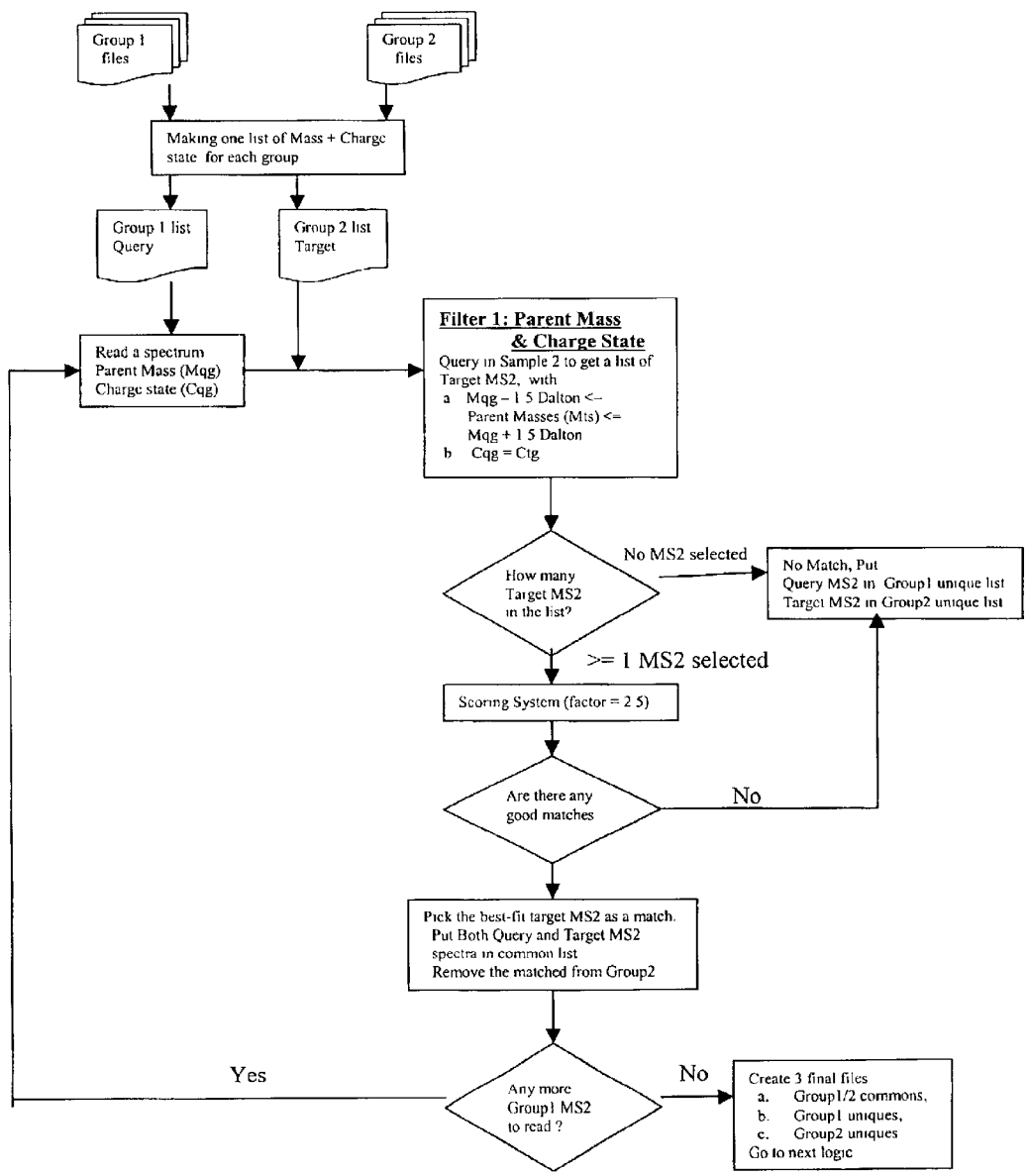
FIG. 4 is a flow chart of inter group pattern matching.

Referring now in general to the Figures, input data (DTA's) are obtained from a mass spectrometer, such as a Finnigan, or the like MS, that is converted into an ASCII format. The DTA can be obtained from software bundled with the particular MS, such as Sequest, Qstar, Sonar, and so forth. The MS or software may include noise reduction provisions particular to the MS device for normalization of the DTA. The DTA collected include MS spectrum data for a specific ion, or peptide, and in particular the Parent Mass and Charge State, and the daughter ion mass and intensity pairs to form a working file.

For data preparation, daughter peak merging is performed by merging all daughter ions ejected within the range of ±0.3 Dalton. It is well known that the machine reading of the mass of an ion, both parent ions and daughter ions, produces variations. Variations claimed by manufacturers is ±0.3 dalton, however, variations of ±1.5 daltons has been observed in parent masses and variations of ±1 daltons has been observed in daughter ion masses. Thus, daughter ions which drop in the same range are considered the same daughter ions as it is very rare for two different daughter ions from b and y series to have masses so close. A list is created of all daughter ions that are represented by only one charge state wherein the different charge state does not change the daughter composition, and the scan number is the same.

The parent ions in each sample are then merged with adjacent scan number and the differences of the masses of the parent ion drop within the range of about 0.5–1.0 Dalton. The above principles are used to create a working file for each sample which contains detailed data of all DTA's, including DTA file name and scan number, parent mass and charge state, and a list of the daughter ion masses and intensity pairs.

Daughter ion subtraction takes place between a first query sample (Sample1) compared to a second sample (Target). The working file, previously generated as defined above, is read for each of the parent ions in Query DTA (qi) to obtain parent mass (Mqi) and charge state (Cqi). The Target working file is queried with both Mqi and Cqi, to obtain the target DTA list (T1–Tm) with their parent masses (Mt1–Mtm) drop in the range of Mqi±1.5 Dalton, and their charge states (Ct1–Ctm) is the same to Cqi:

$Mtj=Mqi\pm1.5$ Dalton $Ctj=Cqi$ Where $1\leq j\leq m$

Qi is compared with each of the Tj in T1–Tm list of daughter patterns. If no match is found, the query MS2 is placed in a unique list. If a match is found, the match is filtered by comparison by a scoring system.

In the scoring system, each daughter ion (Qik) in Qi is compared to the whole list of daughters (Tj1–Tjn) in Tj. It is considered as a match, and Qik and Tjg will be removed from Qi and Tj, respectively, if $||Qik\text{-}Tjg||\leq\pm1$ Dalton, where $1\leq g\leq n$ The match is awarded a score based on the following scheme (for partition=4):

Score=5, if $|Qik\text{-}Tjg|\leq\pm0.25$ Dalton;
Score=4, if $|Qik\text{-}Tjg|\leq\pm0.50$ Dalton;
Score=2, if $|Qik\text{-}Tjg|\leq\pm0.75$ Dalton;
Score=1, if $|Qik\text{-}Tjg|\leq\pm1.00$ Dalton.

The comparison will provide the following values:
a. S: cumulative score;
b. Q_ratio: matched/Total_Query ratio;
c. T_ratio: matched/Total_Target ratio;
d. t_score=3*((Q_ratio+T_ratio)/2)*Rs
   Rs: acceptable ratio (in %) of matched over total.

The comparison will be considered as a pattern match candidate, to be included into the list of matched candidates QT, if the following conditions are met:
a. S>t_score;
b. Total_Target>Td and Total_Query>Td;
c. 1≤Total_Query or Total_Query/Total_Target≤2.

If the QT list contains a single candidate, then take this candidate as the match and remove Qi and Ti from Query and Target list, respectively.

If the QT list contains more than one match candidates, the list is filtered to find a match by the following method:
a. Calculate DQT:

DQT=Medium (Scan_Qi)–Medium (Scan_Tj)
Note: scan number for a DTA can be a range.
b. Compare DQT to Standard DQT between the samples by trend:

DQT=Scan_Q1–Scan_T1 or
DQT=Scan_Qi–Scan_Tj.
Where Scan_Qi and Scan_Tj are considered the best match between two samples. If DQT>1 and Dqt<1, then it is likely that Tj belongs to a different peptide and Tj is to be removed from QT list.
c. Compare Dqt to FQT between the sample by distance:
FQT=k*((Scan_Qi+Scan_Tj)/2)
Where k is the slope of a linear function Scan_QT=f(dqt)= k*dqt+b. The function of f(dqt) is proximated to linear correlation.

d. Choose the Tj with the highest score Sj from remaining QT list to be the final match.

Figure 5:
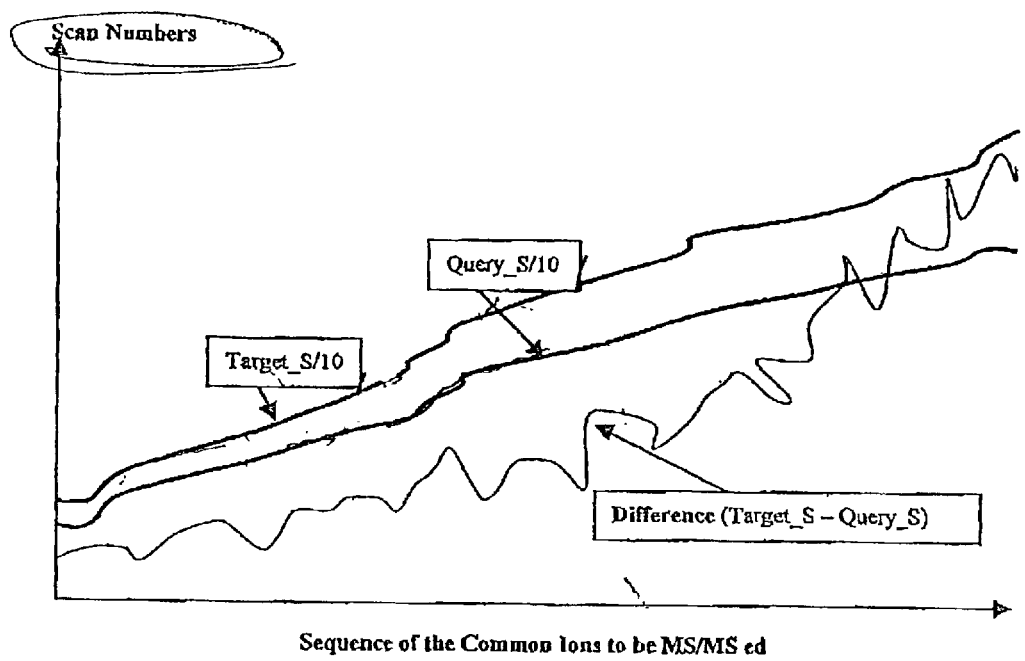
FIG. 5 is a chart comparing scan numbers versus sequence of the common ions to be MS/MS.

It should be noted that each of the DTA's have a specific scan number, which is the indication when an ion has been out of a column and analyzed by MS/MS. The sequence of a scan number for a sample is fairly stable. However, the scan numbers shift between sample runs. If there is the same ion in both samples to be compared, scan number of this ion in one of the samples will differ from another sample. The distance of this same ion in two samples is the function of the scan numbers, in the range of 20 (scan number 600)–400 (scan number 4000). FIG. 5 depicts a typical curve drawn with the data from extracted common ions from two samples as discussed in this disclosure.

After all the Query DTAs have been used for comparisons, a consensus file is generated which contains the common ions between the two samples. Files are generated for ions unique to each sample:
a. sample12_common (each matched ions' DTA names, parent masses, charge states, pattern daughters).
b. sample1_unique;
c. sample2_unique.

5. Within each group, pairing samples in all possible ways to the pairwise comparison as above. The total number of the comparison is given out by:

$$\sum_{l=n}^{2}(l-1)$$

Where n is the number of samples with the group.

The sample12_common files are merged and, and hash all the entries (pair matches) with parent mass+charge state. Cluster all the entries on their parent mass+charge state, with variation of ±1.5 Dalton. So, the members of each clusters are considered the candidates for extended matches outside of the original pairwise matches.

Daughter ion pattern comparison is performed within each of the clusters on the pattern daughter ions. The ratio Rc(the matched sample #/Total sample #) is then calculated. The ion will be included in the final group_common list if:

$Rc\geq Rm$

If there is any mismatch within the cluster, then create another cluster to include them. Rc is calculated for each of these sub-clusters, and evaluated as follows:

$Rc\geq Rm$

One file is generated for each group:
Groupx_whole (uniques+commons), which should contain:
DTA names(s), parent mass, charge state, all daughter ions.

The scoring system is repeated to compare the 2 final group files. The final files generated are:
a. Group1_unique;
b. Group2_unique;
c. Group12_common.

The 3 DTA directories are reconstructed based on the above files. The DTA reconstruction should be:
a. Recover all the DTAs with different charge states;
b. For each DTA, recover original data format;
c. For each DTA, recover original file name;
d. Create supporting files for software (e.g. SEQUEST, QStar) search.

The software bundled with the MS can be further used to compare the peptide sequences among those single ions. This allows the uncharacterized ions to be reviewed in view of their correlation among those ions tagged with the same peptide sequence. The sequences predicated by the bundled program, such as SEQUEST, is not of interest in this step, rather, the correlations are of interest. Further, the sequences predicated along with the protein name associated with the sequence provide research assistance.

The SEQUEST Search allows further filtering: However, instead of having M*N number of SEQUEST searches, there are only 3 summary results:

a. One for common ones, which is optional, for reference;
b. One for Group1;
c. One for Group2.

2. Subtracting Group1 and Group2 summary files on protein names generates files:

a. Group1_unique_with_name;
b. Group2 unique_with_name;
c. Group1_unique_without_name;
d. Group2_unique_without_name.

Group_unique_without_name list should be used for optional databases searches, e.g., with 6 reading frame databases.

Group_unique_with_name list can be used directly for further analysis, including data mining.

EXAMPLE 1

Unique Proteins in Control Group.

---

Proteins sharing keywords with the subtracted.

(Format: Protein name and IDs: Keywords)
gi|2258128|emb|CAA69 complement 9 [*homo sapiens*] [mass = 60398]: complement
C05ADEE16G02.0791.0793.2.dta
C05ADEE16G02.2549.2549.3.dta
C05ADEE16G02.2537.2539.2.dta
0145ADEE17G02.2909.2909.2.dta
C05ADEE16G02.1803.1805.2.dta
C05ADEE16G02.1666.1676.2.dta
0145ADEE17G02.2064.2074.2.dta
0154ADEE16G02.2064.2064.2.dta
C05ADEE16G02.2062.2064.2.dta
0154ADEE16G02.2235.2239.2.dta The Rest of the Unique Proteins.

gi|223002|prf||04011: fibrin beta [*homo sapiens*] [mass = 50763]
C05ADEE16G02.2294.2324.2.dta
C05ADEE16G02.1281.1283.2.dta
C07ADEE16G02.1281.1284.2.dta
C07ADEE16G02.1581.1587.3.dta
C07ADEE16G02.2310.2312.2.dta
0154ADEE16G02.2672.2690.2.dta
C05ADEE16G02.0811.0813.3.dta
C07ADEE16G02.0811.0813.3.dta
0145ADEE17G02.2665.2667.2.dta
0145ADEE17G02.1962.1964.2.dta
0145ADEE17G02.1217.1223.3.dta
0145ADEE17G02.1219.1221.2.dta
C07ADEE16G02.1219.1221.2.dta
0154ADEE16G02.1206.1208.2.dta
0145ADEE17G02.1203.1205.2.dta
0154ADEE16G02.1721.1723.3.dta
C07ADEE16G02.0797.0801.2.dta
C05ADEE16G02.0807.0809.2.dta
C07ADEE16G02.1343.1345.2.dta
0145ADEE17G02.1012.1014.2.dta
0154ADEE16G02.1959.1961.2.dta
C05ADEE16G02.1959.1961.2.dta -continued Summary list, refer above for IDs and DTA files.

complement 9 [*homo sapiens*] [mass = 60398]
fibrin beta [*homo sapiens*] [mass = 50763]

EXAMPLE 2

Unique Single Ions in Control Group.

---

Unique Single Ions in Control Group, With Multiple Samples Matches For Peptide

| | |
|---|---|
| 2: | ADSQAQLLLSTVVGVFTAPGLHLK gi\|15079348 |
| | C05ADEE16G02.2824.2832.3.dta |
| | C07ADEE16G02.2834.2834.2.dta |
| 3: | AEMEVQMMKKELDQK gi\|17563838 |
| | C05ADEE16G02.0916.0918.3.dta |
| | C07ADEE16G02.0918.0920.3.dta |
| | 0145ADEE17G02.1321.1323.3.dta |
| 2: | ALDRHQNSPAPR gi\|20544433 |
| | C07ADEE16G02.1363.1363.2.dta |
| | 0154ADEE16G02.1751.1753.2.dta |
| 3: | ALFATSTAGLLRCPR gi\|21229522 |
| | C07ADEE16G02.0643.0643.3.dta |
| | C05ADEE16G02.0647.0649.3.dta |
| | 0154ADEE16G02.1033.1035.3.dta |
| 2: | ANELIKLVGLEGK gi\|16080327 |
| | 0145ADEE17G02.2463.2469.1.dta |
| | 0154ADEE16G02.2468.2470.2.dta |
| 2: | APVAGLSGAAGGSTLYSFEAK gi\|21244270 |
| | C05ADEE16G02.2391.2391.3.dta |
| | 0145ADEE17G02.2487.2487.2.dta |
| 2: | AQEGPDAEIIGGERSVFYLLMK gi\|12644073 |
| | C05ADEE16G02.1730.1732.3.dta |
| | 0145ADEE17G02.2126.2128.3.dta |
| 2: | ASDSVQSALKNR gi\|15238480 |
| | C07ADEE16G02.1036.1038.3.dta |
| | C05ADEE16G02.1038.1038.3.dta |
| 2: | ASLTRTPPTASLTR gi\|18594161 |
| | C05ADEE16G02.1712.1714.2.dta |
| | C07ADEE16G02.1720.1722.2.dta |
| 3: | CLDSVLGEFAFPDEFVVE gi\|7522626 |
| | C05ADEE16G02.2296.2314.3.dta |
| | C07ADEE16G02.2328.2358.3.dta |
| | 0154ADEE16G02.2698.2700.3.dta |
| 2: | DALTGHLRTHSVGKPHK gi\|1911483 |
| | C05ADEE16G02.1837.1841.3.dta |
| | 0145ADEE17G02.2230.2234.3.dta |
| 2: | DAVKFGRMSK gi\|1082764 |
| | C05ADEE16G02.1503.1507.2.dta |
| | 0154ADEE16G02.1893.1895.2.dta |
| | C05ADEE16G02.1893.1895.2.dta |
| 2: | DEINSLIGQKNVLFFK gi\|15896245 |
| | C07ADEE16G02.1465.1465.2.dta |
| | 0145ADEE17G02.1849.1849.2.dta |
| 2: | DRVLMGPARTGGR gi\|17554264 |
| | C05ADEE16G02.1255.1265.2.dta |
| | 0154ADEE16G02.1651.1665.2.dta |
| 2: | DWLFSLKISEVK gi\|20502693 |
| | C07ADEE16G02.0787.0793.2.dta |
| | 0145ADEE17G02.1199.1199.2.dta |
| 2: | DYIFGNYIER gi\|10092579 |
| | C05ADEE16G02.1630.1632.2.dta |
| | C07ADEE16G02.1641.1643.2.dta |
| 2: | EGTIGDMAILGITESFQVKR gi\|11493524 |
| | C05ADEE16G02.2136.2188.3.dta |
| | 0154ADEE16G02.2562.2564.3.dta |
| 2: | EHLVQATPENLQEAR gi\|10092579 |
| | C07ADEE16G02.0853.0857.3.dta |
| | C05ADEE16G02.0864.0864.3.dta |
| 2: | EKVLAYK gi\|19913514 |
| | C07ADEE16G02.1914.1914.1.dta |
| | 0145ADEE17G02.2294.2294.1.dta |
| 2: | ELINYNAFARDFK gi\|8250394 |

-continued

Unique Single Ions in Control Group, With Multiple Samples Matches For Peptide

|   |   |
|---|---|
|   | C05ADEE16G02.1877.1887.2.dta |
|   | 0145ADEE17G02.2274.2274.2.dta |
| 2: | EMEVYRVTESLQR gi\|14249254 |
|   | 0154ADEE16G02.1979.1981.2.dta |
|   | 0145ADEE17G02.1984.1988.2.dta |
| 2: | EPNNNIGRKH gi\|17440552 |
|   | C05ADEE16G02.1235.1245.2.dta |
|   | C07ADEE16G02.1239.1239.2.dta |
| 2: | FSAEALRCHPR gi\|29389 |
|   | C05ADEE16G02.2003.2005.2.dta |
|   | C07ADEE16G02.2014.2016.2.dta |
| 3: | GALAQAQEVSLGADVGRNPR gi\|17474963 |
|   | 0145ADEE17G02.2380.2380.2.dta |
|   | C05ADEE16G02.2503.2507.3.dta |
|   | C07ADEE16G02.2523.2525.3.dta |
| 2: | GDGTDGVGSMPCGR gi\|18580732 |
|   | 0154ADEE16G02.1528.1528.2.dta |
|   | 0145ADEE17G02.1529.1531.2.dta |
|   | C05ADEE16G02.1529.1531.2.dta |
| 2: | GEVQAMLGQSTEELR gi\|1480096 |
|   | C05ADEE16G02.1362.1384.2.dta |
|   | 0154ADEE16G02.1739.1739.2.dta |
| 3: | GHPFLQEECKAPAR gi\|20550933 |
|   | C05ADEE16G02.1024.1026.3.dta |
|   | 0154ADEE16G02.1030.1030.3.dta |
|   | C07ADEE16G02.1030.1030.3.dta |
|   | 0145ADEE17G02.1430.1435.3.dta |
| 2: | GLLDQGIPSK gi\|18375646 |
|   | C07ADEE16G02.1157.1157.3.dta |
|   | 0154ADEE16G02.1552.1552.3.dta |
| 2: | GLRKMLDNFDCFGDK gi\|20380096 |
|   | 0145ADEE17G02.1241.1241.3.dta |
|   | C05ADEE16G02.1241.1241.3.dta |
|   | C07ADEE16G02.1241.1241.3.dta |
|   | 0145ADEE17G02.1639.1639.3.dta |
|   | 0154ADEE16G02.1639.1639.3.dta |
|   | C07ADEE16G02.1639.1639.3.dta |
| 2: | GLVLVVGSTGSGKSTSLASMIDHR gi\|14090413 |
|   | C07ADEE16G02.1175.1181.3.dta |
|   | C05ADEE16G02.1186.1190.3.dta |
| 2: | GVAVLHIGGGSEVEVNEK gi\|17864606 |
|   | 0154ADEE16G02.1172.1174.3.dta |
|   | C05ADEE16G02.1172.1174.3.dta |
|   | 0145ADEE17G02.1173.1175.3.dta |
| 2: | GWQVYGLALDSDTAPTLR gi\|21243805 |
|   | C05ADEE16G02.0807.0809.3.dta |
|   | 0154ADEE16G02.1206.1208.3.dta |
| 2: | GWRPYEIHSVTPIDEILNMFK gi\|8923754 |
|   | C05ADEE16G02.1616.1618.3.dta |
|   | C07ADEE16G02.1635.1637.3.dta |
| 2: | HAQEELPPPPPQKKR gi\|118685 |
|   | C07ADEE16G02.0839.0841.3.dta |
|   | C05ADEE16G02.0848.0848.3.dta |
| 2: | HLALGCFGLNR gi\|16805179 |
|   | C07ADEE16G02.0877.0879.2.dta |
|   | C05ADEE16G02.0884.0886.2.dta |
| 2: | HTWSLLKEMAK gi\|11493656 |
|   | C05ADEE16G02.2300.2306.1.dta |
|   | C05ADEE16G02.2698.2700.2.dta |
| 2: | IARNIYIKVGEDQVFPPK gi\|20535619 |
|   | C05ADEE16G02.2051.2057.3.dta |
|   | C07ADEE16G02.2062.2074.3.dta |
| 2: | ILAITFTKK gi\|12045098 |
|   | 0154ADEE16G02.2259.2265.2.dta |
|   | C05ADEE16G02.2328.2328.1.dta |
| 2: | KEGDGKGK gi\|12843573 |
|   | C05ADEE16G02.0920.0922.2.dta |
|   | 0145ADEE17G02.1327.1329.2.dta |
|   | 0154ADEE16G02.1327.1329.2.dta |
| 4: | LAALSTATTVHHQSQHAVTTCYGR gi\|20891466 |
|   | C05ADEE16G02.2401.2423.2.dta |
|   | C07ADEE16G02.2423.2439.3.dta |
|   | 0145ADEE17G02.2761.2763.3.dta |
|   | 0145ADEE17G02.2783.2783.2.dta |
| 2: | LAGRILGMGDVASLAEK gi\|3024639 |
|   | C05ADEE16G02.2393.2397.2.dta |

-continued

Unique Single Ions in Control Group, With Multiple Samples Matches For Peptide

|   |   |
|---|---|
|   | 0154ADEE16G02.2778.2784.2.dta |
| 2: | LAPPPVAELR gi\|3915680 |
|   | C07ADEE16G02.0970.0976.2.dta |
|   | 0154ADEE16G02.1374.1376.2.dta |
| 2: | LLWLVLQPFFYSLR gi\|18583655 |
|   | C05ADEE16G02.2017.2019.3.dta |
|   | 0145ADEE17G02.2400.2404.3.dta |
| 2: | LNNGEITQHR gi\|29565 |
|   | C07ADEE16G02.0580.0583.2.dta |
|   | C05ADEE16G02.0584.0586.2.dta |
| 2: | LRGEAAAGAAGMKR gi\|17939383 |
|   | C07ADEE16G02.0680.0680.2.dta |
|   | 0154ADEE16G02.1081.1081.2.dta |
| 2: | LSSLTPCPN gi\|8922394 |
|   | 0154ADEE16G02.1107.1109.2.dta |
|   | 0145ADEE17G02.1108.1108.2.dta |
| 3: | LSWLEGGVR gi\|15643398 |
|   | C07ADEE16G02.0783.0783.2.dta |
|   | C05ADEE16G02.0784.0789.2.dta |
|   | 0154ADEE16G02.1186.1196.2.dta |
| 2: | MGGAAWDGEKLSVGSGK gi\|20473307 |
|   | C05ADEE16G02.1047.1066.3.dta |
|   | 0154ADEE16G02.1452.1456.3.dta |
| 2: | MGPTTSPVPR gi\|20541193 |
|   | 0145ADEE17G02.1261.1263.2.dta |
|   | C05ADEE16G02.1261.1263.2.dta |
|   | C07ADEE16G02.1265.1267.2.dta |
| 2: | MLAPSGSSGVWR gi\|6912282 |
|   | C05ADEE16G02.0518.0520.2.dta |
|   | 0154ADEE16G02.0898.0900.2.dta |
| 2: | MQLVDHRGGGGGGGKGGR gi\|13787204 |
|   | 0145ADEE17G02.1024.1024.3.dta |
|   | 0154ADEE16G02.1024.1024.3.dta |
|   | C07ADEE16G02.1024.1024.3.dta |
|   | 0154ADEE16G02.1421.1421.3.dta |
| 2: | NGWLNLEFENR gi\|20541427 |
|   | C07ADEE16G02.2062.2074.2.dta |
|   | 0154ADEE16G02.2434.2436.2.dta |
| 2: | NPIVLSMYFTKQLYR gi\|14733277 |
|   | C05ADEE16G02.1146.1146.2.dta |
|   | 0145ADEE17G02.1537.1537.2.dta |
| 2: | NYADQISRLEERESEMK gi\|10432429 |
|   | C05ADEE16G02.1446.1450.3.dta |
|   | C07ADEE16G02.1455.1457.3.dta |
| 2: | PERVLIIGGGDGGVVR gi\|10945607 |
|   | C05ADEE16G02.1078.1078.3.dta |
|   | C07ADEE16G02.1092.1092.3.dta |
| 2: | PIENRILILPSVTR gi\|1071965 |
|   | C07ADEE16G02.0735.0737.3.dta |
|   | 0145ADEE17G02.1137.1143.3.dta |
| 2: | PSIPQQEHTAVAKHGPTEKTLR gi\|20553669 |
|   | C05ADEE16G02.0774.0776.3.dta |
|   | 0154ADEE16G02.1176.1182.3.dta |
| 3: | QEHDLVFAVR gi\|21243872 |
|   | C05ADEE16G02.2409.2409.1.dta |
|   | C07ADEE16G02.2419.2421.2.dta |
|   | 0145ADEE17G02.2755.2781.1.dta |
| 2: | RILNRLQPR gi\|17456789 |
|   | C07ADEE16G02.0605.0605.3.dta |
|   | 0154ADEE16G02.0996.0998.3.dta |
| 3: | RIMVITVSLIMLR gi\|14042829 |
|   | C07ADEE16G02.1042.1044.3.dta |
|   | C05ADEE16G02.1043.1045.3.dta |
|   | 0154ADEE16G02.1446.1474.3.dta |
| 2: | RLGSVQR gi\|20551188 |
|   | C07ADEE16G02.0597.0599.2.dta |
|   | C05ADEE16G02.0598.0600.2.dta |
| 2: | RPAPSGGASGDLRAFGTR gi\|1082358 |
|   | C07ADEE16G02.0580.0583.3.dta |
|   | C05ADEE16G02.0584.0586.3.dta |
| 2: | RQDELIVLNVSGR gi\|14739334 |
|   | C07ADEE16G02.2998.3006.2.dta |
|   | C05ADEE16G02.3002.3002.2.dta |
| 3: | RQQMQDFFLAHK gi\|10952524 |
|   | C07ADEE16G02.0623.0627.3.dta |
|   | C05ADEE16G02.0633.0637.3.dta |

-continued

Unique Single Ions in Control Group, With Multiple Samples Matches For Peptide

|   |   |
|---|---|
| 2: | 0145ADEE17G02.1032.1034.3.dta<br>RSPTGSTTSRASTVSTK gi\|7513102<br>C05ADEE16G02.1110.1144.3.dta<br>0154ADEE16G02.1522.1546.3.dta |
| 2: | RYNLSLLQTLMFNSARMSFR gi\|18978275<br>C07ADEE16G02.1968.1972.3.dta<br>0154ADEE16G02.2341.2351.3.dta |
| 2: | SAFKAVLHQPLKVIR gi\|7662659<br>C05ADEE16G02.1503.1507.3.dta<br>0145ADEE17G02.1511.1513.3.dta<br>C07ADEE16G02.1511.1513.3.dta |
| 2: | SEAEDASLLSFMQGYMK gi\|224917<br>C07ADEE16G02.2192.2192.3.dta<br>0154ADEE16G02.2546.2552.2.dta |
| 2: | SGSYSYLEERK gi\|21360806<br>C07ADEE16G02.0936.0938.2.dta<br>C05ADEE16G02.0941.0943.2.dta |
| 3: | SIVHPSYNSNTLNNDIMLIK gi\|15988427<br>C07ADEE16G02.1517.1519.3.dta<br>C07ADEE16G02.1673.1673.3.dta<br>0145ADEE17G02.1908.1910.2.dta |
| 2: | SNDMNWAHRASR gi\|106716<br>C05ADEE16G02.2136.2188.2.dta<br>0145ADEE17G02.2567.2583.2.dta |
| 4: | SPLGEEMR gi\|2392352<br>C05ADEE16G02.0821.0823.2.dta<br>C07ADEE16G02.0821.0823.2.dta<br>C05ADEE16G02.0832.0832.2.dta<br>0145ADEE17G02.1227.1229.2.dta<br>0154ADEE16G02.1228.1230.2.dta<br>C05ADEE16G02.1228.1230.2.dta |
| 2: | SQNDFDLVPWLQIATQLISK gi\|1154664<br>C05ADEE16G02.1068.1070.3.dta<br>C07ADEE16G02.1070.1072.3.dta |
| 2: | SSSVGCLAEASAR gi\|10047175<br>C0154ADEE16G02.1222.1224.2.dta<br>0145ADEE17G02.1225.1225.2.dta<br>C07ADEE16G02.1225.1225.2.dta |
| 3: | TATSEYQTFFNPR gi\|1335344<br>0145ADEE17G02.1406.1408.2.dta<br>C05ADEE16G02.1406.1408.2.dta<br>C07ADEE16G02.1415.1421.2.dta<br>0145ADEE17G02.1812.1812.2.dta |
| 2: | TMGYSQEIVEK gi\|20562022<br>C05ADEE16G02.2009.2009.1.dta<br>0145ADEE17G02.2388.2390.1.dta |
| 2: | TSPSNSKNICMPTTDNNNNSSSSTDDTK gi\|256818<br>C05ADEE16G02.0973.0979.3.dta<br>0145ADEE17G02.1381.1381.3.dta |
| 2: | TVFPGAVPVLPASPPPK gi\|10864047<br>C07ADEE16G02.0849.0855.3.dta<br>0145ADEE17G02.1356.1358.2.dta<br>0154ADEE16G02.1356.1358.2.dta<br>C05ADEE16G02.1356.1358.2.dta |
| 2: | VESLFLDERMSLTQRIGK gi\|17457181<br>C05ADEE16G02.0842.0842.3.dta<br>0154ADEE16G02.1238.1240.3.dta |
| 2: | VGFYESDVMGR gi\|17455493<br>C07ADEE16G02.1290.1290.2.dta<br>0145ADEE17G02.1683.1683.2.dta<br>C07ADEE16G02.1683.1683.2.dta |
| 2: | VIEMVTNLVNINTNK gi\|20543383<br>C05ADEE16G02.1320.1320.2.dta<br>C07ADEE16G02.1331.1331.2.dta |
| 2: | VIERYMPRAFGR gi\|11499504<br>C05ADEE16G02.1738.1738.2.dta<br>0154ADEE16G02.2139.2145.2.dta |
| 2: | VLNPPATFLYR gi\|21232394<br>C07ADEE16G02.1265.1267.3.dta<br>0145ADEE17G02.1657.1659.3.dta |
| 3: | VLLPQVGKLFKK gi\|6322590<br>C07ADEE16G02.0747.0751.3.dta<br>C05ADEE16G02.0753.0753.3.dta<br>0154ADEE16G02.1153.1155.3.dta |
| 3: | VTVAGIEQRFCQQCSR gi\|15227896<br>C05ADEE16G02.0960.0964.3.dta |

-continued

Unique Single Ions in Control Group, With Multiple Samples Matches For Peptide

|   |   |
|---|---|
|   | C07ADEE16G02.0966.0968.3.dta<br>0145ADEE17G02.1366.1368.3.dta<br>0154ADEE16G02.1366.1368.3.dta |
| 2: | VVIAPAGITHDPR gi\|21233290<br>C07ADEE16G02.2328.2358.2.dta<br>0145ADEE17G02.2671.2673.2.dta |
| 3: | WEQLIAFK gi\|6759114<br>C05ADEE16G02.1871.1873.1.dta<br>C07ADEE16G02.1894.1896.1.dta<br>0145ADEE17G02.2260.2264.1.dta |
| 2: | WQQGHQLAIMKGFQK gi\|12834350<br>0154ADEE16G02.1278.1280.3.dta<br>C05ADEE16G02.1484.1486.3.dta |
| 2: | YEDKTCPLKK gi\|16080632<br>C05ADEE16G02.0928.0928.1.dta<br>0145ADEE17G02.1340.1340.1.dta |
| 2: | YLKAIR gi\|21242998<br>C05ADEE16G02.0878.0880.1.dta<br>0145ADEE17G02.1279.1279.1.dta |
| 2: | YSKLKEK gi\|13431562<br>C05ADEE16G02.0462.0466.2.dta<br>0154ADEE16G02.0560.0562.2.dta |
| 2: | YTWHEATLGK gi\|11065769<br>C07ADEE16G02.0637.0637.3.dta<br>0154ADEE16G02.1010.1010.3.dta |
| 3: | Apolipoprotein e [homo sapiens]<br>C05ADEE16G02.2062.2064.3.dta<br>0145ADEE17G02.2066.2068.2.dta<br>C05ADEE16G02.2066.2068.2.dta<br>C07ADEE16G02.2082.2082.2.dta |
| 1: | Hypothetical protein xp_106741 [homo sapiens]<br>C05ADEE16G02.0938.0951.3.dta |
| 1: | Similar to glyceraldehyde 3-phosphate dehydrogenase, liver [homo sapiens]<br>0145ADEE17G02.2757.2759.3.dta |

EXAMPLE 3

Proteins and Single Ions Subtracted by Either Pattern Matching or Word Matching

Protein subtracted based on both pattern-matching and IDs.

gi|11761629|ref|NP_0: a-alpha fibrinogen [homo sapiens]
gi|178345|gb|AAA9879: alloalbumin venezia [homo sapiens] [mass = 69227]
gi|4502149|ref|NP_00: apolipoprotein a-ii precursor [homo sapiens]
gi|178730|gb|AAB0048: apolipoprotein b-100 precursor [homo sapiens] [mass = 515558]
gi|178855|gb|AAA5176: apolipoprotein j precursor [homo sapiens] [mass = 48803]
gi|1314244|gb|AAA997: complement c4b precursor [homo sapiens] [mass = 188405]
gi|20545719|ref|XP_0: complement component 3 precursor [homo sapiens] [mass = 187148]
gi|14577919|ref|NP_0: complement component 4a preproprotein; acidic c4; rodgers form of c4; complement component 4s [homo sapiens] [mass = 192336]
gi|1070458|pir||KUHU: ferroxidase (ec 1.16.3.1) precursor - human [mass = 122652]
gi|223918|prf||10043: fibrinogen alphaa [homo sapiens] [mass = 49397]
gi|20178280|sp|P0267: fibrinogen gamma chain precursor (pro2061)
gi|11761631|ref|NP_0: fibrinogen, beta chain preproprotein; fibrinogen, b beta polypeptide
gi|16933542|ref|NP_0: fibronectin 1, isoform 1 preproprotein; cold-insoluble globulin
gi|1212947|emb|CAA25: haptoglobin [homo sapiens] [mass = 38452]
gi|11435220|ref|XP_0: inter-alpha (globulin) inhibitor, h1 polypeptide [*homo sapiens*]
gi|125000|sp|P19823|: inter-alpha-trypsin inhibitor heavy chain
h2 precursor (iti heavy chain h2) hyaluronan-associated protein)
(shap)
gi|229479|prf||74052: lipoprotein gln i [*homo sapiens*]
gi|178775|gb|AAA5174: proapolipoprotein [*homo sapiens*]
[mass = 28962]
gi|20551100|ref|XP_0: similar to dj34f7.4 (complement component
4a) [*homo sapiens*]

Protein subtracted based on names.

No Match with the same name, but different IDs

Common Single Ions Between Patient and Control Groups

| | |
|---|---|
| AKRELSQGISK: | gi|20471541 |
| patient: | 2 |
| | 12ADEE15G02.0958.0960.2.dta |
| | 18ADEE16G02.0978.0980.2.dta |
| control: | 2 |
| | C07ADEE16G02.0966.0968.2.dta |
| | 0145ADEE17G02.1366.1368.2.dta |
| | 0154ADEE16G02.1366.1368.2.dta |
| APKPKAAK: | gi|4885377 |
| patient: | 3 |
| | 31ADEE16G02.0685.0689.2.dta |
| | 20ADEE16G02.0698.0700.2.dta |
| | 18ADEE16G02.0705.0707.2.dta |
| control: | 2 |
| | C07ADEE16G02.0700.0702.2.dta |
| | 0145ADEE17G02.1100.1102.2.dta |
| EALAKGK: | gi|4885231 |
| patient: | 3 |
| | 12ADEE15G02.0655.0655.2.dta |
| | 20ADEE16G02.0668.0670.2.dta |
| | 18ADEE16G02.0679.0681.2.dta |
| control: | 2 |
| | C05ADEE16G02.0670.0674.2.dta |
| | 0154ADEE16G02.1071.1073.2.dta |
| EHVDVIAK: | gi|20544347 |
| patient: | 2 |
| | 31ADEE16G02.1267.1271.1.dta |
| | 18ADEE16G02.1293.1293.1.dta |
| control: | 3 |
| | C05ADEE16G02.1285.1287.1.dta |
| | C07ADEE16G02.1286.1288.1.dta |
| | 0154ADEE16G02.1679.1681.1.dta |
| FEDGVLDPDYPR: | gi|139653 |
| patient: | 3 |
| | 20ADEE16G02.1301.1303.2.dta |
| | 31ADEE16G02.1306.1312.2.dta |
| | 12ADEE15G02.1325.1327.2.dta |
| | 18ADEE16G02.1325.1327.2.dta |
| control: | 2 |
| | C05ADEE16G02.1316.1318.2.dta |
| | 0145ADEE17G02.1725.1725.2.dta |
| FEEHKNEKDMAK: | gi|4894370 |
| patient: | 3 |
| | 2ADEE15G02.1523.1552.2.dta |
| | 12ADEE15G02.1556.1558.2.dta |
| | 20ADEE16G02.1556.1558.2.dta |
| | 18ADEE16G02.1563.1563.2.dta |
| control: | 2 |
| | 0145ADEE17G02.1561.1563.2.dta |
| | 0154ADEE16G02.1561.1563.2.dta |
| | C05ADEE16G02.1561.1563.2.dta |
| | C07ADEE16G02.1571.1575.2.dta |
| FSEMQNERR: | gi|21361704 |
| patient: | 2 |
| | 20ADEE16G02.2009.2015.2.dta |
| | 20ADEE16G02.2021.2023.2.dta |
| | 31ADEE16G02.2021.2023.2.dta |
| control: | 2 |
| | C05ADEE16G02.2017.2019.2.dta |
| | 0145ADEE17G02.2400.2404.2.dta |
| HTLNQIDEVK: | gi|2521981 |
| patient: | 3 |
| | 20ADEE16G02.0766.0768.2.dta |
| | 18ADEE16G02.0772.0774.2.dta |
| | 31ADEE16G02.0773.0773.2.dta |
| control: | 2 |
| | 0154ADEE16G02.1172.1174.2.dta |
| | C05ADEE16G02.1172.1174.2.dta |
| | 0145ADEE17G02.1173.1175.2.dta |
| LDDIVDSVLATGIQR: | gi|11359042 |
| patient: | 2 |
| | 12ADEE15G02.1735.1735.2.dta |
| | 18ADEE16G02.1735.1735.2.dta |
| | 31ADEE16G02.1740.1746.2.dta |
| control: | 2 |
| | C05ADEE16G02.1730.1732.2.dta |
| | C07ADEE16G02.1744.1744.2.dta |
| PAERGLPAPK: | gi|1076013 |
| patient: | 4 |
| | 20ADEE16G02.1865.1869.2.dta |
| | 12ADEE15G02.1870.1874.2.dta |
| | 31ADEE16G02.1873.1877.2.dta |
| | 18ADEE16G02.1873.1879.2.dta |
| control: | 3 |
| | C05ADEE16G02.1867.1869.2.dta |
| | C07ADEE16G02.1886.1892.2.dta |
| | 0145ADEE17G02.2256.2258.2.dta |
| QVVTFVVLLSLCLLK: | gi|18572033 |
| patient: | 2 |
| | 18ADEE16G02.1373.1377.3.dta |
| | 12ADEE15G02.1377.1381.3.dta |
| control: | 3 |
| | C05ADEE16G02.1378.1386.3.dta |
| | C07ADEE16G02.1379.1383.3.dta |
| | 0145ADEE17G02.1774.1786.3.dta |
| TYLPAVDEK: | gi|114022 |
| patient: | 2 |
| | 31ADEE16G02.0957.0959.2.dta |
| | 18ADEE16G02.0982.0984.2.dta |
| control: | 3 |
| | C07ADEE16G02.0972.0974.2.dta |
| | C05ADEE16G02.0975.0977.2.dta |
| | 0154ADEE16G02.1380.1380.2.dta |
| | C05ADEE16G02.1380.1380.2.dta |
| YVDKAILGDEDDMFR: | gi|11499013 |
| patient: | 2 |
| | 18ADEE16G02.1781.1785.3.dta |
| | 12ADEE15G02.1786.1788.3.dta |
| control: | 3 |
| | C05ADEE16G02.1789.1791.3.dta |
| | C07ADEE16G02.1796.1798.3.dta |
| | 0145ADEE17G02.2180.2182.3.dta |

Alpha2-hs glycoprotein [*homo sapiens*]

| | |
|---|---|
| patient: | 4 |
| | 18ADEE16G02.1261.1263.3.dta |
| | 31ADEE16G02.1261.1263.3.dta |
| | 31ADEE16G02.0764.0766.2.dta |
| | 18ADEE16G02.1235.1237.3.dta |
| | 31ADEE16G02.1235.1237.3.dta |
| | 12ADEE15G02.1252.1254.3.dta |
| control: | 3 |
| | C05ADEE16G02.1255.1265.3.dta |
| | 0145ADEE17G02.1649.1651.3.dta |
| | C07ADEE16G02.1261.1269.3.dta |

Angiotensinogen (serine (or cysteine) proteinase inhibitor, clade a

| | |
|---|---|
| patient: | 3 |
| | 18ADEE16G02.1625.1625.2.dta |
| | 20ADEE16G02.1604.1606.2.dta |
| | 31ADEE16G02.2238.2242.2.dta |
| control: | 6 |
| | C05ADEE16G02.2234.2236.2.dta |
| | C07ADEE16G02.2260.2260.3.dta |
| | C07ADEE16G02.2828.2830.3.dta |
| | 0145ADEE17G02.2611.2613.2.dta |
| | 0145ADEE17G02.2617.2617.3.dta |
| | 0145ADEE17G02.3185.3187.3.dta |

Chain a, crystal structure of benzamidine inhibited bovine pancreatic trypsin at modelled

| | |
|---|---|
| patient: | 3 |
| | 18ADEE16G02.1523.1527.2.dta |

-continued

|  |  |
|---|---|
| control: | 31ADEE16G02.1395.1397.2.dta<br>12ADEE15G02.1415.1415.2.dta<br>2<br>0154ADEE16G02.1917.1917.2.dta<br>C07ADEE16G02.1523.1532.2.dta |

Complement component 5 [*homo sapiens*]

|  |  |
|---|---|
| patient: | 3<br>18ADEE16G02.3297.3299.3.dta<br>31ADEE16G02.3339.3341.3.dta<br>12ADEE15G02.3317.3325.3.dta |
| control: | 2<br>C05ADEE16G02.3354.3356.3.dta<br>C07ADEE16G02.3354.3358.3.dta |

Ig heavy chain - human

|  |  |
|---|---|
| patient: | 1<br>18ADEE16G02.0768.0770.2.dta<br>31ADEE16G02.0768.0770.2.dta |
| control: | 3<br>C05ADEE16G02.0774.0776.2.dta<br>C07ADEE16G02.0765.0767.2.dta<br>0154ADEE16G02.1176.1182.2.dta |

Lipoprotein ciii [*homo sapiens*]

|  |  |
|---|---|
| patient: | 1<br>18ADEE16G02.2158.2166.2.dta |
| control: | 5<br>C05ADEE16G02.0953.0955.2.dta<br>C05ADEE16G02.2170.2178.2.dta<br>C07ADEE16G02.0948.0954.2.dta<br>0145ADEE17G02.2551.2555.2.dta<br>0145ADEE17G02.1356.1358.2.dta<br>0154ADEE16G02.1356.1358.2.dta<br>C05ADEE16G02.1356.1358.2.dta |

Vitronectin precursor (serum spreading factor) (s-protein) (v75)
[contains: vitronectin v65 subunit; vitronectin v10 subunit;
somatomedin b]

|  |  |
|---|---|
| patient: | 4<br>18ADEE16G02.1257.1257.3.dta<br>18ADEE16G02.2076.2076.2.dta<br>18ADEE16G02.1233.1233.3.dta<br>31ADEE16G02.1233.1233.3.dta<br>12ADEE15G02.1315.1321.2.dta |
| control: | 3<br>0154ADEE16G02.1641.1645.3.dta<br>0145ADEE17G02.1251.1253.3.dta<br>C05ADEE16G02.1251.1253.3.dta<br>C07ADEE16G02.1257.1257.3.dta |

Common Single Ions Between Patient and Common Groups

| KTYSPAKYGK: | gi|5174563 |
|---|---|
| patient: | 2<br>20ADEE16G02.0683.0685.2.dta<br>12ADEE15G02.0693.0695.2.dta<br>18ADEE16G02.0693.0695.2.dta |
| common: | 2<br>12ADEE15G02.0659.0661.2.dta<br>0154ADEE16G02.1085.1087.2.dta |
| MCDNCCKDSAFERTNITEYCR: | gi|1172898 |
| patient: | 2<br>20ADEE16G02.1687.1687.3.dta<br>18ADEE16G02.1693.1693.3.dta |
| common: | 3<br>C07ADEE16G02.1716.1718.3.dta<br>0154ADEE16G02.2084.2084.3.dta<br>0145ADEE17G02.2090.2096.3.dta |

Common Single Ions Between Control and Common Groups

| FKGYYKIAR: | gi|17933636 |
|---|---|
| control: | 2<br>0154ADEE16G02.1272.1274.3.dta<br>0145ADEE17G02.1275.1281.3.dta |
| common: | 2<br>C07ADEE16G02.0869.0873.3.dta<br>C05ADEE16G02.0872.0874.3.dta |
| MAEMLVQLVRRIEK: | gi|13385746 |
| control: | 2 |

-continued

|  |  |
|---|---|
|  | C07ADEE16G02.0686.0688.3.dta<br>C05ADEE16G02.0689.0691.3.dta |
| common: | 2<br>12ADEE15G02.0659.0661.3.dta<br>0154ADEE16G02.1085.1087.3.dta |

EXAMPLE 4

Unique Proteins in Patient Group

Proteins sharing keywords with the subtracted.

(Format: Protein name and IDs: Keywords)
gi|178853|gb|AAB5939 apolipoprotein e [*homo sapiens*]
[mass = 36207]: apolipoprotein
31ADEE16G02.2065.2067.2.dta
12ADEE15G02.2002.2002.2.dta
12ADEE15G02.0677.0679.2.dta
31ADEE16G02.0677.0679.2.dta
20ADEE16G02.1184.1190.2.dta
18ADEE16G02.1201.1215.2.dta
31ADEE16G02.2061.2063.3.dta
18ADEE16G02.1361.1361.2.dta
18ADEE16G02.1028.1028.2.dta
31ADEE16G02.1028.1030.2.dta
31ADEE16G02.2007.2011.2.dta
12ADEE15G02.0781.0781.2.dta
31ADEE16G02.0781.0781.2.dta
12ADEE15G02.1015.1015.2.dta
20ADEE16G02.1015.1017.2.dta
18ADEE16G02.1990.1996.2.dta
20ADEE16G02.1350.1352.2.dta
18ADEE16G02.0719.0725.2.dta
18ADEE16G02.0689.0689.2.dta
31ADEE16G02.0685.0689.2.dta
18ADEE16G02.2048.2056.2.dta
12ADEE15G02.0781.0781.2.dta
31ADEE16G02.0781.0781.2.dta
12ADEE15G02.1011.1013.2.dta
20ADEE16G02.1013.1013.2.dta
18ADEE16G02.2046.2050.3.dta
12ADEE15G02.2000.2000.2.dta
12ADEE15G02.0867.0867.2.dta
18ADEE16G02.0867.0869.2.dta
20ADEE16G02.0867.0869.2.dta The Rest of the Unique Proteins.

gi|577055|emb|CAA249: gamma-fibrinogen chain fragment [*homo sapiens*] [mass = 7031]
18ADEE16G02.1453.1461.2.dta
31ADEE16G02.1427.1429.2.dta
12ADEE15G02.1439.1455.2.dta
20ADEE16G02.1440.1442.2.dta
gi|17066105|emb|CAD1: titin [*homo sapiens*] [mass = 3816218]
12ADEE15G02.0948.0950.2.dta
20ADEE16G02.0941.0943.2.dta
12ADEE15G02.0937.0939.2.dta
18ADEE16G02.0937.0939.2.dta
31ADEE16G02.0937.0939.2.dta
18ADEE16G02.1565.1572.3.dta
31ADEE16G02.1913.1915.3.dta
12ADEE15G02.0532.0534.3.dta
18ADEE16G02.1755.1761.3.dta
12ADEE15G02.1260.1262.3.dta
31ADEE16G02.1089.1119.2.dta
12ADEE15G02.1556.1558.2.dta
20ADEE16G02.1556.1558.2.dta Summary list, refer above for IDs and DTA files.

apolipoprotein e [*homo sapiens*] [mass = 36207]
gamma-fibrinogen chain fragment [*homo sapiens*] [mass = 7031]
titin [*homo sapiens*] [mass = 3816218]

EXAMPLE 5

Unique Single Ions in Patient Group

Unique Single Ions in Patient Group, With Multiple Sample Matches For Peptides

| | | |
|---|---|---|
| 2: | AADDTWEPFASGK | gi\|2135953 |
| | 12ADEE15G02.1383.1383.2.dta | |
| | 18ADEE16G02.1391.1395.2.dta | |
| 2: | AAKGAKPEPAPAPPPPGAK | gi\|18598655 |
| | 31ADEE16G02.0826.0828.3.dta | |
| | 20ADEE16G02.0833.0835.3.dta | |
| 2: | AEDTAVYYCARDIQLDAFDIWGQ | gi\|13171474 |
| | 18ADEE16G02.1411.1411.3.dta | |
| | 20ADEE16G02.1411.1411.3.dta | |
| | 31ADEE16G02.1411.1411.3.dta | |
| | 18ADEE16G02.1425.1427.3.dta | |
| 2: | AETVIIGGGCVGVSLAYHLAKAGMK | gi\|7019365 |
| | 20ADEE16G02.1937.1943.3.dta | |
| | 31ADEE16G02.1949.1951.3.dta | |
| 2: | APAAAEMLLRSKS | gi\|17451900 |
| | 31ADEE16G02.2297.2347.2.dta | |
| | 12ADEE15G02.2304.2306.2.dta | |
| | 18ADEE16G02.2304.2306.2.dta | |
| 2: | APLARLHPPIK | gi\|21244563 |
| | 18ADEE16G02.2376.2380.1.dta | |
| | 31ADEE16G02.2399.2401.1.dta | |
| 2: | APWIPPNPTSPLASPKCAAWLKVK | gi\|7512882 |
| | 12ADEE15G02.0937.0939.3.dta | |
| | 18ADEE16G02.0937.0939.3.dta | |
| | 31ADEE16G02.0937.0939.3.dta | |
| | 20ADEE16G02.0941.0943.3.dta | |
| 2: | CCGGTVIQTQACTPSR | gi\|18584772 |
| | 20ADEE16G02.1060.1062.3.dta | |
| | 18ADEE16G02.1071.1079.3.dta | |
| 2: | DINYVNPVIK | gi\|14735486 |
| | 20ADEE16G02.1231.1235.2.dta | |
| | 12ADEE15G02.1240.1240.2.dta | |
| 2: | DKEFLVFETSDIAISLKWLVEDIK | gi\|12045184 |
| | 20ADEE16G02.2495.2497.3.dta | |
| | 31ADEE16G02.2549.2551.3.dta | |
| 3: | DKVILLDETLNAIATELKPR | gi\|13508310 |
| | 31ADEE16G02.0843.0853.3.dta | |
| | 12ADEE15G02.0851.0855.3.dta | |
| | 18ADEE16G02.0871.0873.3.dta | |
| | 20ADEE16G02.0871.0873.3.dta | |
| 2: | DSALSTPRAELAQQWFVLALR | gi\|21231993 |
| | 20ADEE16G02.1174.1176.3.dta | |
| | 12ADEE15G02.1188.1192.3.dta | |
| 2: | DVEGDSVPK | gi\|20482245 |
| | 31ADEE16G02.0817.0822.2.dta | |
| | 18ADEE16G02.0827.0829.2.dta | |
| | 20ADEE16G02.0827.0829.2.dta | |
| 2: | DVWGIEGPIDAAFTR | gi\|139653 |
| | 20ADEE16G02.2049.2053.2.dta | |
| | 31ADEE16G02.2083.2087.2.dta | |
| 2: | DYWSTVK | gi\|224917 |
| | 31ADEE16G02.1034.1036.1.dta | |
| | 12ADEE15G02.1054.1060.2.dta | |
| 2: | EGAGSSALK | gi\|10436629 |
| | 31ADEE16G02.0904.0908.2.dta | |
| | 20ADEE16G02.0915.0917.2.dta | |
| 2: | EHSGTRLHPCTRCTVK | gi\|20548673 |
| | 31ADEE16G02.1762.1766.2.dta | |
| | 18ADEE16G02.1773.1773.2.dta | |
| 2: | ENLSPEDFK | gi\|15668768 |
| | 12ADEE15G02.0722.0722.2.dta | |
| | 20ADEE16G02.0729.0735.2.dta | |
| 2: | EPAEKPGLGR | gi\|11498871 |
| | 20ADEE16G02.0939.0945.2.dta | |
| | 18ADEE16G02.0962.0964.2.dta | |
| 2: | EQGISLANVVPHK | gi\|7435945 |
| | 31ADEE16G02.0813.0813.3.dta | |
| | 12ADEE15G02.0819.0819.3.dta | |
| | 20ADEE16G02.0819.0819.3.dta | |
| 2: | GPEGIGKPGAAGAPGQPGIPGTK | gi\|18105032 |
| | 20ADEE16G02.1440.1442.3.dta | |
| | 18ADEE16G02.1453.1461.3.dta | |

-continued

Unique Single Ions in Patient Group, With Multiple Sample Matches For Peptides

| | | |
|---|---|---|
| 2: | GQPKDATDWCCQKHDCCYAHLK | gi\|7242177 |
| | 18ADEE16G02.2382.2386.3.dta | |
| | 31ADEE16G02.2393.2395.3.dta | |
| 2: | GSPAINVAVHVFR | gi\|1336728 |
| | 20ADEE16G02.1354.1356.2.dta | |
| | 12ADEE15G02.1356.1356.2.dta | |
| 2: | GWVTDGFSSLK | gi\|224917 |
| | 12ADEE15G02.1590.1594.2.dta | |
| | 12ADEE15G02.1592.1592.1.dta | |
| 2: | HQLVVSSPPR | gi\|14783228 |
| | 18ADEE16G02.1737.1745.2.dta | |
| | 20ADEE16G02.1743.1743.2.dta | |
| 2: | IDDLFDQLKGARVFSK | gi\|6002795 |
| | 20ADEE16G02.1821.1823.3.dta | |
| | 18ADEE16G02.1833.1835.3.dta | |
| | 20ADEE16G02.1833.1835.3.dta | |
| 2: | IELEHSIGAIQHSLSR | gi\|16077314 |
| | 20ADEE16G02.1436.1438.3.dta | |
| | 18ADEE16G02.1447.1447.3.dta | |
| 2: | KAVVARK | gi\|9827811 |
| | 12ADEE15G02.0929.0929.2.dta | |
| | 20ADEE16G02.0949.0949.2.dta | |
| | 31ADEE16G02.0949.0949.2.dta | |
| 2: | KIILTESYCKSELCILSTQTR | gi\|18595923 |
| | 12ADEE15G02.0781.0781.3.dta | |
| | 31ADEE16G02.0781.0781.3.dta | |
| | 20ADEE16G02.0792.0794.3.dta | |
| 2: | KSIKIDDLK | gi\|16804979 |
| | 18ADEE16G02.0845.0845.2.dta | |
| | 20ADEE16G02.0845.0845.2.dta | |
| | 18ADEE16G02.0853.0853.2.dta | |
| 2: | LAAQLFSNTTANAIR | gi\|422517 |
| | 31ADEE16G02.1163.1171.2.dta | |
| | 12ADEE15G02.1176.1210.2.dta | |
| 2: | LAMRGYPMLTTMCPGPQKK | gi\|20546026 |
| | 12ADEE15G02.0821.0825.3.dta | |
| | 18ADEE16G02.0835.0839.3.dta | |
| 2: | LGALNSSLQLLEDRLHQLSLK | gi\|14043093 |
| | 12ADEE15G02.0795.0795.3.dta | |
| | 31ADEE16G02.0795.0795.3.dta | |
| | 20ADEE16G02.0798.0800.3.dta | |
| 2: | LHEMNKHEETVSVAMR | gi\|20468266 |
| | 12ADEE15G02.1040.1040.3.dta | |
| | 31ADEE16G02.1040.1040.3.dta | |
| | 20ADEE16G02.1049.1058.3.dta | |
| 2: | LIEPICPQFAEYVWRK | gi\|8569090 |
| | 20ADEE16G02.1709.1709.2.dta | |
| | 12ADEE15G02.1723.1723.2.dta | |
| 2: | LIQLKPQEEETHDEIFGGLSKVHQK | gi\|20482517 |
| | 18ADEE16G02.1931.1931.3.dta | |
| | 12ADEE15G02.1934.1934.3.dta | |
| 2: | LLLNKSASAQNELMLLDMLK | gi\|19115107 |
| | 20ADEE16G02.1013.1013.3.dta | |
| | 12ADEE15G02.1015.1015.3.dta | |
| 2: | LMDQNLK | gi\|14010352 |
| | 12ADEE15G02.0915.0915.1.dta | |
| | 20ADEE16G02.0919.0919.1.dta | |
| 2: | LQKAIEEEEARMR | gi\|11360154 |
| | 20ADEE16G02.0927.0929.3.dta | |
| | 18ADEE16G02.0943.0945.3.dta | |
| | 31ADEE16G02.0943.0945.3.dta | |
| 2: | LSDAEPEVR | gi\|20480773 |
| | 20ADEE16G02.0776.0778.2.dta | |
| | 18ADEE16G02.0784.0786.2.dta | |
| 2: | LSILTEK | gi\|20546459 |
| | 12ADEE15G02.0564.0566.1.dta | |
| | 20ADEE16G02.0634.0636.1.dta | |
| 2: | LTLIEKPCPR | gi\|18558922 |
| | 20ADEE16G02.1663.1665.2.dta | |
| | 18ADEE16G02.1677.1681.2.dta | |
| 2: | MTSSFHGIRPPQLEQPEKMPVLK | gi\|12839853 |
| | 20ADEE16G02.1273.1275.3.dta | |
| | 12ADEE15G02.1280.1282.3.dta | |
| 2: | NAMRVTLDATGNEGSWLFIQPFWK | gi\|17366458 |
| | 12ADEE15G02.0805.0815.3.dta | |
| | 18ADEE16G02.0814.0820.3.dta | |

Unique Single Ions in Patient Group, With Multiple Sample Matches For Peptides

| | | |
|---|---|---|
| 2: | NGDDSDNGDGADVK gi\|11061640 | |
| | 20ADEE16G02.1281.1281.3.dta | |
| | 12ADEE15G02.1287.1289.3.dta | |
| 2: | NIAQFGEMIRLKTGR gi\|346690 | |
| | 18ADEE16G02.2124.2124.2.dta | |
| | 12ADEE15G02.2134.2138.2.dta | |
| 2: | NIHFSWDILAK gi\|11078753 | |
| | 12ADEE15G02.2294.2298.1.dta | |
| | 18ADEE16G02.2318.2322.1.dta | |
| 2: | NLLENLSGGSTFK gi\|2129238 | |
| | 31ADEE16G02.0748.0748.2.dta | |
| | 18ADEE16G02.0761.0761.2.dta | |
| 2: | NPAIFGFLLSAK gi\|6319547 | |
| | 12ADEE15G02.1025.1027.3.dta | |
| | 12ADEE15G02.1044.1046.3.dta | |
| | 18ADEE16G02.1044.1046.3.dta | |
| 2: | PLTTSPAPAPPPR gi\|14747828 | |
| | 20ADEE16G02.1047.1053.2.dta | |
| | 12ADEE15G02.1052.1056.2.dta | |
| 2: | PSGNSSSGGKIWQGEPARVR gi\|5453900 | |
| | 31ADEE16G02.0748.0748.3.dta | |
| | 18ADEE16G02.0761.0761.3.dta | |
| 2: | PSPQRNTTNDIAHIQNEEIMSLQMK gi\|20554181 | |
| | 20ADEE16G02.1910.1925.3.dta | |
| | 12ADEE15G02.1922.1924.3.dta | |
| 2: | QDFTVKTVSGER gi\|20470381 | |
| | 12ADEE15G02.0807.0809.3.dta | |
| | 20ADEE16G02.0807.0809.3.dta | |
| | 18ADEE16G02.0812.0812.3.dta | |
| 2: | QDMIVRTTQEKLK gi\|20070257 | |
| | 18ADEE16G02.0845.0845.3.dta | |
| | 20ADEE16G02.0845.0845.3.dta | |
| | 18ADEE16G02.0853.0853.3.dta | |
| 4: | QIFSILAATPGVQVEK gi\|11061648 | |
| | 31ADEE16G02.1087.1097.3.dta | |
| | 12ADEE15G02.1108.1110.3.dta | |
| | 20ADEE16G02.1112.1116.3.dta | |
| | 18ADEE16G02.1126.1136.3.dta | |
| 2: | QPTQEEILFQVAQAGEVDK gi\|1708635 | |
| | 20ADEE16G02.1156.1160.3.dta | |
| | 12ADEE15G02.1167.1169.3.dta | |
| 2: | QPVPAGVVPGVVYER gi\|21233559 | |
| | 18ADEE16G02.1833.1835.3.dta | |
| | 20ADEE16G02.1833.1835.3.dta | |
| | 12ADEE15G02.1840.1840.3.dta | |
| 2: | QTDEQLHRMGAPR gi\|21241051 | |
| | 20ADEE16G02.1739.1741.2.dta | |
| | 31ADEE16G02.1853.1855.2.dta | |
| 2: | QYEQNIMDHKLNLDLLTQSTSSSR gi\|20536830 | |
| | 18ADEE16G02.1656.1662.3.dta | |
| | 12ADEE15G02.1661.1661.3.dta | |
| 2: | RDRAPFVFTSDMAYVINGGDK gi\|13632400 | |
| | 31ADEE16G02.0621.0623.3.dta | |
| | 18ADEE16G02.0637.0639.3.dta | |
| 2: | RIADLRSDLGPEIR gi\|21230680 | |
| | 12ADEE15G02.1731.1739.1.dta | |
| | 18ADEE16G02.1731.1757.1.dta | |
| 4: | SKEQLTPLIK gi\|4502149 | |
| | 31ADEE16G02.0912.0914.2.dta | |
| | 20ADEE16G02.0933.0935.2.dta | |
| | 20ADEE16G02.0949.0949.3.dta | |
| | 31ADEE16G02.0949.0949.3.dta | |
| | 18ADEE16G02.0949.0952.3.dta | |
| 2: | SLPWSAARQLR gi\|21231002 | |
| | 12ADEE15G02.0439.0441.3.dta | |
| | 31ADEE16G02.0499.0501.3.dta | |
| 2: | SLSLAQNLLER gi\|18560704 | |
| | 20ADEE16G02.1074.1096.2.dta | |
| | 18ADEE16G02.1091.1120.2.dta | |
| 3: | SPELQAEAK gi\|4502149 | |
| | 12ADEE15G02.0612.0614.2.dta | |
| | 20ADEE16G02.0612.0614.2.dta | |
| | 12ADEE15G02.0616.0618.1.dta | |
| | 31ADEE16G02.0635.0637.1.dta | |
| 4: | SSGTSYPDVLK gi\|15988427 | |
| | 31ADEE16G02.0975.0977.2.dta | |
| | 20ADEE16G02.0987.0989.2.dta | |
| | 12ADEE15G02.0991.0993.2.dta | |
| | 18ADEE16G02.1004.1010.2.dta | |
| 2: | SSQSVLYSSNSK gi\|1730075 | |
| | 18ADEE16G02.1992.1994.2.dta | |
| | 31ADEE16G02.2013.2015.2.dta | |
| 3: | SSSRPKVSATAAAAAGK gi\|8250399 | |
| | 20ADEE16G02.1019.1021.2.dta | |
| | 12ADEE15G02.1038.1038.1.dta | |
| | 18ADEE16G02.1040.1042.2.dta | |
| 2: | TIENSQCTKVEEDFNLATKIISK gi\|13469731 | |
| | 31ADEE16G02.2254.2256.3.dta | |
| | 20ADEE16G02.2262.2266.3.dta | |
| 2: | TQLQSFSQYIENRPEMK gi\|17441098 | |
| | 31ADEE16G02.1445.1457.3.dta | |
| | 12ADEE15G02.1451.1453.3.dta | |
| 2: | VAVARAQGLGGQLR gi\|21231008 | |
| | 18ADEE16G02.2338.2342.2.dta | |
| | 31ADEE16G02.2371.2371.2.dta | |
| 3: | VEGNEVIIENFIGEK gi\|11499493 | |
| | 18ADEE16G02.2280.2282.2.dta | |
| | 31ADEE16G02.2285.2287.2.dta | |
| | 31ADEE16G02.2291.2311.1.dta | |
| 4: | VKSPELQAEAK gi\|4502149 | |
| | 12ADEE15G02.0645.0647.2.dta | |
| | 12ADEE15G02.0651.0653.2.dta | |
| | 31ADEE16G02.0651.0653.2.dta | |
| | 20ADEE16G02.0658.0660.2.dta | |
| | 18ADEE16G02.0667.0669.2.dta | |
| | 31ADEE16G02.0667.0669.2.dta | |
| 3: | VPGPAFGHQIAYCNLLPR gi\|20538746 | |
| | 31ADEE16G02.0881.0885.3.dta | |
| | 20ADEE16G02.0891.0895.3.dta | |
| | 18ADEE16G02.0904.0906.3.dta | |
| 2: | VYVSLGALKMHIRTHTLPCK gi\|399449 | |
| | 31ADEE16G02.2469.2505.3.dta | |
| | 18ADEE16G02.2482.2486.3.dta | |
| 2: | YIHTGEK gi\|13374557 | |
| | 20ADEE16G02.0893.0893.2.dta | |
| | 12ADEE15G02.0893.0895.2.dta | |
| 2: | YWITADK gi\|19115051 | |
| | 12ADEE15G02.1042.1050.1.dta | |
| | 18ADEE16G02.1057.1059.1.dta | |
| 6: | Apolipoprotein a-ii precursor [*homo sapiens*] | |
| | 12ADEE15G02.0925.0927.2.dta | |
| | 20ADEE16G02.2683.2685.2.dta | |
| | 31ADEE16G02.0659.0663.3.dta | |
| | 31ADEE16G02.2745.2759.2.dta | |
| | 31ADEE16G02.2753.2765.3.dta | |
| | 31ADEE16G02.2904.2918.3.dta | |
| 1: | C9 complement protein [*homo sapiens*] | |
| | 18ADEE16G02.1799.1799.2.dta | |
| 1: | Chain c, crystal structure of the human alpha-thrombin-haemadin complex: an exosite ii-binding inhibitor | |
| | 20ADEE16G02.1436.1438.2.dta | |
| 1: | Gvp1 gene in phh1 homolog [*rhizobium rhizogenes*] | |
| | 18ADEE16G02.1749.1751.3.dta | |
| 1: | Prothrombin [*homo sapiens*] | |
| | 20ADEE16G02.1401.1405.2.dta | |
| | 31ADEE16G02.1401.1405.2.dta | |

The examples illustrate the summarization of Group1_unique with_name; Group2 unique_with_name; Group1_unique_without_name and Group2_unique_without_name; wherein Group_unique_without name list is used for optional databases searches, and Group unique_with_name list is used directly for further analysis such as data mining.

It is to be understood that while we have illustrated and described certain forms of our invention, it is not to be limited to the specific forms or arrangement of the steps herein described and shown. It will be apparent to those skilled in the art that various changes may be made without departing from the scope of the invention and the invention is not to be considered limited to what is shown in the drawings and described in the specification.

Although the instant invention has been exemplified in the context of an ion-trap device, it is to be understood that the sample mass may be analyzed by any combination of ionization and mass spectrometer. The ionization method may include, but is not limited to such methods as electron ionization, chemical ionization, fast atom bombardment, desorption chemical ionization, plasmadeorption, thermospray, atmospheric pressure chemical ionization, MALDI or electrospray ionization (ESI) Principally the ionization method will be MALDI or ESI.

Prior art mass spectrometer formats are known to be useful either singly or in various combinations for use in analyzing translation products. These formats may include, but are not limited to, ionization (I) techniques, including but not limited to matrix assisted laser desorption (MALDI), continuous or pulsed electrospray (ESI) and related methods (e.g., IONSPRAY or THERMOSPRAY), or massive cluster impact (MCI); these ion sources can be matched with detection formats including linear or non-linear reflection time-of-flight (TOF), single or multiple quadrupole, single or multiple magnetic sector, Fourier Transform ion cyclotron resonance (FTICR), ion trap, and combinations thereof (e.g., ion-trap/time-of-flight). For ionization, numerous matrix/wavelength combinations (MALDI) or solvent combinations (ESI) can be employed. Subattomole levels of protein have been detected, for example, using ESI (Valaskovic, G. A. et al., (1996) Science 273:1199–1202) or MALDI (Li, L. et al., (1996) J. Am. Chem. Soc. 118:1662–1663) mass spectrometry. ES mass spectrometry has been introduced by Fenn et al. (J. Phys. Chem. 88, 4451–59 (1984); PCT Application No. WO 90/14148) and current applications are summarized in recent review articles (R. D. Smith et al., Anal. Chem. 62, 882–89 (1990) and B. Ardrey, Electrospray Mass Spectrometry, Spectroscopy Europe, 4, 10–18 (1992)). MALDI-TOF mass spectrometry has been introduced by Hillenkamp et al. ("Matrix Assisted UV-Laser Desorption/Ionization: A New Approach to Mass Spectrometry of Large Biomolecules," Biological Mass Spectrometry (Burlingame and McCloskey, editors), Elsevier Science Publishers, Amsterdam, pp. 49–60, 1990). With ESI, the determination of molecular weights in femtomole amounts of sample is very accurate due to the presence of multiple ion peaks which all could be used for the mass calculation.

With regard to electrospray, an electrospray is produced by applying a strong electric field under atmospheric pressure to a liquid passing through a capillary tube with a weak flux. The electric field is obtained by applying a potential difference of 3–6 kV between the capillary and the counter electrode separate by 0.3 to 2 cm producing electric fields of the order of 10 E6 V per cm. This field induces a charge at the liquid surface located at the end of capillary, which will break to form highly charged droplets. A gas injected co-axially at a low flow rate allows the dispersion of the spray to be limited in space. These droplets then pass either through a curtain of heated inert gas, most often nitrogen, or through a heated capillary to remove the last solvent molecules." See for example "Mass spectrometry, principle and application" 2nd edition. 2001. Edmond de Hoffmann and Vincent Stroobant. John Wiley & Sons, New York. Page 35.

With regard to the mass spectrometer, per se, there are several types of tandem mass spectrometers that could be used to generate the patterns of MS/MS spectra that are the substrate for the program. These mass spectrometers generate both parent ions in the +1 (MALDI and ESI) and the +2, +3, +4 etc charge state (ESI). The program takes the charge state of the parent into consideration as part of the data associated with the parent ion. The types of mass analyzer mass analyzers include the quadropole, octopole, ion trap or QUISTOR, time of flight (TOF) Time of Flight with reflectron, the Fourier transformed ion cyclotron resonance (FTICR also called FTMS), magnetic and electromagnetic sector. The tandem mass spectrometer mass consist of the homogenous or heterogenous combination of two or more of any of these devices in any order (Hybrid instrument). The fragmentation method may include post source decay of the parent ion or its fragment, or collision-activated or collision-induced decomposition of the parent ions, or fragment ions, or metastable ions with a relatively immobile target such as gas molecules or other parent or fragment ions, or photons or electrons or solid objects. The combinations may preferentially include the quadropole or octopole ion trap, the Quadropole-Quadropole (DC and rf or rf only)-TOF, the ion trap-FTMS, the TOF-TOF, the ion trap-TOF, or the TOF-PSD-TOF.

The signal resulting from the instrument may be mathematically transformed or filtered. The MASS analyzer may be directly or indirectly coupled to a number of devices, which are illustrated by, but not limited to, liquid chromatography or capillary electrophoresis, or free flow electrophoresis, or gel electrophoresis, or multidimensional chromatography, or multidimensional electrophoresis.

What is claimed is:

1. A method for pattern matching between samples of amino acids comprising;

analyzing a sample mass by ionization and mass spectrometry;

merging ions from said sample mass in an inner-sample to form a first group and a control group;

providing a means for matching ions of a similar pattern wherein said means for matching includes comparing samples according to molecular weight by awarding a first Score if a particular daughter ion less list of total daughter ions is $\leq \pm 0.25$ Dalton, a second Score if said daughter ion less said list of total daughter ions is $\leq \pm 0.50$ Dalton, a third Score if said daughter ion less said list of total daughter ions is $\leq \pm 0.75$ Dalton, and a fourth Score if said daughter ion less said list of total daughter ions is $\leq \pm 1.00$ Dalton wherein a pattern match candidate is located if S >t_score; Total_Target >Td and total Query>Td; and $1 \leq$ Total_Query or Total Query/Total_Target$\leq 2$; whereby the comparison has the following values:

a. S: cumulative score;

b. Q_ratio: matched/Total_Query ratio;

c. T_ratio: matched/Total_Target ration;

d. t_score =3*((Q_ratio+T_ratio)/2) * an acceptable ratio of matched over total;

and creating an output data file for use in data mining.

2. The method for pattern matching according to claim 1 including the step of merging daughter ions ejected within the range of about ±0.3 Dalton and recording all ions represented by only one charge state.

3. The method for pattern matching according to claim 1 including the step of creating data directories and regenerating DTA files.

4. The method for pattern matching according to claim 1 wherein said means for matching further includes a means for comparing scan numbers to sequence of common ions to be MS/MS.

5. The method for pattern matching according to claim 1 wherein said means for matching further includes a means for daughter ion subtraction.

6. The method for pattern matching according to claim 3 including a means for word matching of said files.

7. A method for pattern matching unique sequences in multiple samples of amino acids comprising the steps of:
   a. analyzing a sample mass by ionization and mass spectrometry;
   b. creating a working file for each ion analyzed from said sample mass, said working file including a DTA file name, scan number, parent mass and charge state, and a list of daughter ion masses and intensity pairs;
   c. query each working file to obtain the parent mass (Mqi) and charge state (Cqi) for each parent ion (Qi);
   d. query a target working file with said Mqi and said Cqi to obtain target DTA list (T1–Tm) having a parent mass (Mt1–Mtm) drop in the range of Mqi ±1.5 Dalton and a charge state (Ct1–Ctm) equal to Cqi;
   e. comparing Qi with each cf the Tj in T1–Tm list of daughter patterns, wherein daughter ions are a match if $|Qik\text{-}Tigi| \leq \pm$ Dalton, where $1 \leq g \leq n$ and wherein said match is awarded a first Score if $|Qik\text{-}Tjg| \leq \pm 0.25$ Dalton, a second Score if $|Qik\text{-}Tjg| \leq \pm 0.50$ Dalton, a third Score if $|Qik\text{-}Tjg| \leq \pm 0.75$ Dalton, and a fourth Score if $|Qik\text{-}Tjg| \leq \pm 1.00$ Dalton, wherein the comparison is considered a pattern match candidate, to be included in a list of matched candidates QT, if
      i. 5>t_score;
      ii. Total_Target>Td and Total_Query>Td; and
      iii $1 \leq$ Total_Query or Total_Query/Total_Target $\leq 2$; and
   f. removing daughter ions that match, wherein said pattern match candidate can be used directly or used for further analysis in data mining.

8. The method of pattern matching according to claim 7, wherein said working file is formed by merging all daughter ions ejected within the range of ±0.3 Dalton for each sample and recording DTA's represented by only one charge state.

9. A method for pattern matching unique sequences in multiple samples of amino acids comprising the steps of:
   a. analyzing a sample mass by ionization and mass spectrometry;
   b. creating a working file for each ion analyzed from said sample mass, said working file including a DTA file name, scan number, parent mass and charge state, and a list of daughter ion masses and intensity pairs;
   c. query each working file to obtain the parent mass (Mqi) and charge state (Cqi) for each parent ion (Qi);
   d. query a target working file with said Mqi and said Cqi to obtain target DTA list (T1–Tm) having a parent mass (Mt1–Mtm) drop in the range of Mqi±1.5 Dalton and a charge state (Ct1–Ctm) equal to Cqi;
   e. comparing Qi with each of the Tj in T1–Tm list of daughter patterns, wherein daughter ions are a match if $|Qik\text{-}Tjg| \leq \pm$Dalton, where $1 \leq g \leq n$ and wherein said match is awarded a first Score if $|Qik\text{-}Tjg| \leq \pm 0.25$ Dalton, a second Score if $|Qik\text{-}Tjg| \leq \pm 0.50$ Dalton, a third Score if $|Qik\text{-}Tjg| \leq \pm 0.75$ Dalton, and a fourth Score if $|Qik\text{-}Tjg| \leq \pm 1.00$ Dalton, wherein the comparison is considered a pattern match candidate, to be included in a list of matched candidates QT, if
      i. 5>t_score;
      ii. Total_Target>Td and Total_Query>Td; and
      iii. $1 \leq$ Total_Query or Total_Query/Total Target$\leq 2$;
   f. removing daughter ions that match; and
   g. calculating DQT and comparing to a standard DQT between said samples by trend; wherein said pattern match candidate can be used directly or used for further analysis in data mining.

10. A method for pattern matching unique sequences in multiple samples of amino acids comprising the steps of:
    a. analyzing a sample mass by ionization and mass spectrometry;
    b. creating a working file for each ion analyzed from said sample mass, said working file including a DTA file name, scan number, parent mass and charge state, and a list of daughter ion masses and intensity pairs;
    c. query each working file to obtain the parent mass (Mqi) and charge state (Cgi) for each parent ion (Qi);
    d. query a target working file with said Mqi and said Cqi to obtain target DTA list (T1–Tm) having a parent mass (Mt1–Mtm) drop in the range of Mqi±1.5 Dalton and a charge state (Ct1–Ctm) equal to Cqi;
    e. comparing Qi with each of the Tj in T1–Tm list of daughter patterns, wherein daughter ions are a match if $|Qik\text{-}Tjg| \leq \pm$Dalton, where $1 \leq g \leq n$ and wherein said match is awarded a first Score if $|Qik\text{-}Tjg| \leq \pm 0.25$ Dalton, a second Score if $|Qik\text{-}Tjg| \leq \pm 0.50$ Dalton, a third Score if $|Qik\text{-}Tjg| \leq \pm 0.75$ Dalton, and a fourth Score if $|Qik\text{-}Tjg| \leq \pm 1.00$ Dalton, wherein the comparison is considered a pattern match candidate, to be included in a list of matched candidates QT, if
       i. 5>t_score;
       ii. Total_Target>Td and Total_Query>Td; and
       iii. $1 \leq$ Total Query or Total_Query/Total_Target$\leq 2$;
    f. removing daughter ions that match; and
    g. comparing DQT to FQT between a sample by distance; wherein said pattern match candidate can be used directly or used for further analysis in data mining.

11. The method of pattern matching according to claim 7, including the step of pairing samples, wherein the total number of comparisons is defined as:

$$\sum_{l=n}^{2}(l-1).$$

12. The method of pattern matching according to claim 7 including the step of inserting matched patterns into an MS support software program for use in word match comparison of amino acid ions.

13. The method of pattern matching according to claim 7 including the step of reconstructing DTA directories for use in data mining.

14. A method for pattern matching unique sequences in multiple samples of amino acids comprising the steps of:
    a. analyzing a sample mass by ionization and mass spectrometry;
    b. creating a working file for each ion analyzed from said sample mass, said working file including a DTA file name, scan number, parent mass and charge state, and a list of daughter ion masses and intensity pairs;
    c. query each working file to obtain the parent mass (Mqi) and charge state (Cqi) for each parent ion (Qi);
    d. query a target working file with said Mqi and said Cqi to obtain target DTA list (T1–Tm) having a parent mass (Mt1–Mtm) drop in the range of Mqi+1.5 Dalton and a charge state (Ct1–Ctm) equal to Cqi;

e. comparing Qi with each of the Tj in T1–Tm list of daughter patterns, wherein daughter ions are a match if $|Qik-Tjg| \leq \pm Dalton$, where $1 \leq g \leq n$ and wherein said match is awarded a first Score if $|Qik-Tjg| \leq \pm 0.25$ Dalton, a second Score if $|Qik-Tjg| \leq \pm 0.50$ Dalton, a third Score if $|Qik-Tjg| \pm 0.75$ Dalton, and a fourth Score if $|Qik-Tjg| \leq \pm 1.00$ Dalton, wherein the comparison is considered a pattern match candidate, to be included in a list of matched candidates QT, if i. $5 > t\_score$;

ii. Total_Target>Td and Total_Query>Td; and iii $1 \leq$ Total_Query or Total_Query/Total_Target$\leq 2$;

f. removing daughter ions that match; and g. recording common ions having matched candidates between Qi and Tj and separate unmatched candidates into separate files; wherein said pattern match candidate can be used directly or used for further analysis in data mining.

15. The method of pattern matching according to claim 14 including the step of clustering pattern matches by their parent mass and charge state having a variation of $\pm 1.5$ Dalton.

16. A method for pattern matching unique sequences in multiple samples of amino acids comprising the steps of:

a. analyzing a sample mass by ionization and mass spectrometry;

b. creating a working file for each ion analyzed from said sample mass, said working file including a DTA file name, scan number, parent mass and charge state, and a list of daughter ion masses and intensity pairs;

c. comparing scan numbers to a sequence of common ions on a linear scale;

d. query each working file to obtain the parent mass (Mqi) and charge state (Cqi) for each parent ion (Qi);

e. query a target working file with said Mqi and said Cqi to obtain target DTA list (T1–Tin) having a parent mass (Mt1–Mtm) drop in the range of Mqi$\pm 1.5$ Dalton and a charge state (Ct1–Ctm) equal to Cqi;

f. comparing Qi with each of the Tj in T1–Tm list of daughter patterns, wherein daughter ions are a match if $|Qik-Tjg| \leq \pm Dalton$, where $1 \leq g \leq n$ and wherein said match is awarded a first Score if $|Qik-Tjg| \leq \pm 0.25$ Dalton, a second Score if $|Qik-Tjg| \leq \pm 0.50$ Dalton, a third Score if $|Qik-Tjg| \leq \pm 0.75$ Dalton, and a fourth Score if $|Qik-Tjg| \leq \pm 1.00$ Dalton, wherein the comparison is considered a pattern match candidate, to be included in a list of matched candidates QT, if i. $5 > t\_score$;

ii. Total_Target>Td and Total_Query>Td; and iii. $1 \leq$ Total_Query or Total_Query/Total_Target$\leq 2$ and g. removing daughter ions that match, wherein said pattern match candidate can be used directly or used for further analysis in data mining.

* * * * *